(12) United States Patent
Vujadinovic et al.

(10) Patent No.: US 10,744,196 B2
(45) Date of Patent: Aug. 18, 2020

(54) HPV VACCINES

(71) Applicant: Janssen Vaccines & Prevention B.V., Leiden (NL)

(72) Inventors: Marija Vujadinovic, Leiden (NL); Taco Gilles Uil, Amsterdam (NL); Koen Oosterhuis, Haarlem (NL); Jort Vellinga, Leiden (NL); Jerôme Hubertina Henricus Victor Custers, Alphen aan den Rijn (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 0 days.

(21) Appl. No.: 16/316,719

(22) PCT Filed: Jul. 11, 2017

(86) PCT No.: PCT/EP2017/067383
§ 371 (c)(1),
(2) Date: Jan. 10, 2019

(87) PCT Pub. No.: WO2018/011196
PCT Pub. Date: Jan. 18, 2018

(65) Prior Publication Data
US 2019/0240312 A1    Aug. 8, 2019

(30) Foreign Application Priority Data
Jul. 14, 2016  (EP) .................................. 16179394

(51) Int. Cl.
| A61K 39/12 | (2006.01) |
| C07K 14/025 | (2006.01) |
| C07K 14/005 | (2006.01) |
| A61K 39/00 | (2006.01) |

(52) U.S. Cl.
CPC ............ *A61K 39/12* (2013.01); *C07K 14/005* (2013.01); *A61K 2039/5254* (2013.01); *A61K 2039/5256* (2013.01); *A61K 2039/575* (2013.01); *A61K 2039/645* (2013.01); *A61K 2039/70* (2013.01); *C07K 2319/00* (2013.01); *C12N 2710/10022* (2013.01); *C12N 2710/10042* (2013.01); *C12N 2710/20034* (2013.01)

(58) Field of Classification Search
None
See application file for complete search history.

(56) References Cited

U.S. PATENT DOCUMENTS

| 5,057,540 A | 10/1991 | Kensil et al. |
| 5,559,099 A | 9/1996 | Wickham et al. |
| 5,837,511 A | 11/1998 | Falck-Pedersen et al. |
| 5,837,520 A | 11/1998 | Shabram et al. |
| 5,846,782 A | 12/1998 | Wickham et al. |
| 5,851,806 A | 12/1998 | Kovesdi et al. |
| 5,891,690 A | 4/1999 | Massie |
| 5,965,541 A | 10/1999 | Wickham et al. |
| 5,981,225 A | 11/1999 | Kochanek et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,040,174 A | 3/2000 | Imler et al. |
| 6,113,913 A | 9/2000 | Brough et al. |
| 6,225,289 B1 | 5/2001 | Kovesdi et al. |
| 6,261,823 B1 | 7/2001 | Tang et al. |
| 6,485,958 B2 | 11/2002 | Blanche et al. |
| 7,270,811 B2 | 9/2007 | Bout et al. |
| 7,326,555 B2 | 2/2008 | Konz, Jr. et al. |
| 8,932,607 B2 | 1/2015 | Custers et al. |
| 2011/0059135 A1* | 3/2011 | Kovesdi ................. C12N 15/86 424/233.1 |

FOREIGN PATENT DOCUMENTS

| EP | 1230354 A2 | 8/2002 |
| EP | 0853660 B1 | 1/2003 |
| WO | 90/03184 A1 | 4/1990 |
| WO | 90/14837 A1 | 12/1990 |
| WO | 96/11711 A1 | 4/1996 |
| WO | 98/39411 A1 | 9/1998 |
| WO | 98/22588 A3 | 10/1998 |
| WO | 99/12568 A1 | 3/1999 |
| WO | 99/41416 A2 | 8/1999 |
| WO | 00/29024 A1 | 5/2000 |
| WO | 00/32754 A1 | 6/2000 |
| WO | 00/70071 A1 | 11/2000 |
| WO | 01/66137 A1 | 9/2001 |

(Continued)

OTHER PUBLICATIONS

Wu et al. Capsid display of a conserved human papillomavirus L2 peptide in the adenovirus 5 hexon protein: a candidate prophylactic hpv vaccine approach. Virology Journal (2015) 12:140.*
Jagu et al. Concatenated Multitype L2 Fusion Proteins as Candidate Prophylactic Pan-Human Papillomavirus Vaccines. J Natl Cancer Inst 2009;101: 782-792.*
Abbink et al, "Comparative Seroprevalence and Immunogenicity of Six Rare Serotype Recombinant Adenovirus Vaccine Vectors from Subgroups B and D," Journal of Virology, vol. 81, No. 9, pp. 4654-4663 (May 2007).
Altares et al, "Production and Formulation of Adenovirus Vectors," Advances in Biochemical Engineering/ Biotechnology, vol. 99, pp. 193-260 (2005).

(Continued)

*Primary Examiner* — Nianxiang Zou
(74) *Attorney, Agent, or Firm* — Ice Miller LLP

(57) ABSTRACT

The present invention relates to novel vaccines against Human papillomavirus (HPV) infections, based on recombinant capsid-display adenovirus vectors. Described are capsid modified replication deficient adenovirus particles encoding and displaying multiple HPV L2 antigenic fragments, via a minor capsid protein IX, and their use for eliciting an immune response in order to provide protection against infections from multiple HPV types.

25 Claims, 13 Drawing Sheets
Specification includes a Sequence Listing.

(56) References Cited

FOREIGN PATENT DOCUMENTS

| | | |
|---|---|---|
| WO | 02/40665 A2 | 5/2002 |
| WO | 03/049763 A1 | 6/2003 |
| WO | 03/061708 A1 | 7/2003 |
| WO | 03/078592 A2 | 9/2003 |
| WO | 03/104467 A1 | 12/2003 |
| WO | 04/001032 A2 | 12/2003 |
| WO | 04/004762 A1 | 1/2004 |
| WO | 04/020971 A2 | 3/2004 |
| WO | 05/002620 A1 | 1/2005 |
| WO | 05/080556 A3 | 2/2006 |
| WO | 06/108707 A1 | 10/2006 |
| WO | 07/104792 A2 | 9/2007 |
| WO | 07/110409 A1 | 10/2007 |
| WO | 08/140474 A1 | 11/2008 |
| WO | 09/117134 A2 | 9/2009 |
| WO | 10/060719 A1 | 6/2010 |
| WO | 11/045378 A1 | 4/2011 |
| WO | 11/045381 A1 | 4/2011 |
| WO | 11/098592 A1 | 8/2011 |
| WO | 13/135615 A1 | 9/2013 |
| WO | 15/068101 A1 | 5/2015 |

OTHER PUBLICATIONS

Brough et al, "A Gene Transfer Vector-Cell Line System for Complete Functional Complementation of Adenovirus Early Regions E1 and E4," Journal of Virology, vol. 70, No. 9, pp. 6497-6501 (Sep. 1996).

Abrahamsen et al, "Construction of an Adenovirus Type 7a E1A-Vector," Journal of Virology, vol. 71, No. 11, pp. 8946-8951 (Nov. 1997).

Bett et al, "Packaging Capacity and Stability of Human Adenovirus Type 5 Vectors," Journal of Virology, vol. 67, No. 10, pp. 5911-5921 (Oct. 1993).

Bzymek et al, "Instability of repetitive DNA sequences: The role of replication in multiple mechanisms," Proceedings of the National Academy of Sciences of the United States of America, vol. 98, No. 15, pp. 8319-8325 (2001).

Day et al, "A Human Papillomavirus (HPV) In Vitro Neutralization Assay That Recapitulates the In Vitro Process of Infection Provides a Sensitive Measure of HPV L2 Infection-Inhibiting Antibodies," Clinical and Vaccine Immunology, vol. 19, No. 7, pp. 1075-1082 (Jul. 2012).

Forman et al, "Global Burden of Human Papillomavirus and Related Diseases," Vaccine, vol. 30, Supplement, pp. F12-F23 (2012).

Gao et al, "A Cell Line for High-Yield Production of E1-Deleted Adenovirus Vectors without the Emergence of Replication-Competent Virus," Human Gene Therapy, vol. 11, pp. 213-219 (2000).

Goerke et al, "Development of a Novel Adenovirus Purification Process Utilizing Selective Precipitation of Cellular DNA," Biotechnology and Bioengineering, vol. 91, pp. 12-21 (2005).

Seitz et al, "Current Perspectives on HPV Vaccination," Future Virology, vol. 9, No. 7, pp. 633-653 (2014).

Harro et al, "Safety and Immunogenicity of Adenovirus-Vectored Near-Consensus HIV Type 1 Clade B gag Vaccines in Healthy Adults," AIDS Research and Human Retroviruses, vol. 25, No. 1, pp. 103-114 (2009).

Havenga et al, "Novel replication-incompetent adenoviral B-group vectors: high vector stability and yield in PER.C6 cells," Journal of General Virology, vol. 87, pp. 2135-2143 (2006).

Hoganson et al, "Development of a Stable Adenoviral Vector Formulation," Bioprocessing Journal, pp. 43-48 (Mar. 2002).

Karanam et al, "Developing vaccines against minor capsid antigen L2 to prevent papillomavirus infection," Immunology and Cell Biology, vol. 87, pp. 287-299 (2009).

King et al, "Processive proofreading by the adenovirus DNA polymerase. Association with the priming protein reduces exonucleolytic degradation," Nucleic Acids Research, vol. 25, No. 9, pp. 1745-1752 (1997).

Konz et al, "Serotype Specificity of Adenovirus Purification Using Anion-Exchange Chromatography," Human Gene Therapy, vol. 16, pp. 1346-1353 (Nov. 2005).

Konz et al, "Scaleable Purification of Adenovirus Vectors," Methods in Molecular Biology, vol. 434, No. 2, pp. 13-23 (2008).

Muñoz et al, "Against Which Human Papillomavirus Types Shall We Vaccinate and Screen? The International Perspective," International Journal of Cancer, vol. 111, No. 2, pp. 278-285 (2004).

Nan et al, "Development of an Ad7 cosmid system and generation of an Ad7DeltaE1DeltaE3HIVMN env/rev recombinant virus," Gene Therapy, vol. 10, pp. 326-336 (2003).

Parkin et al, "Chapter 2: The burden of HPV-related cancers," Vaccine, vol. 24, Supplement 3, pp. 11-25 (2006).

Richards et al, "Cleavage of the papillomavirus minor capsid protein, L2, at a furan consensus site is necessary for infection," Proceedings of the National Academy of Sciences of the United States of America, vol. 103, No. 5, pp. 1522-1527 (Jan. 2006).

Solabomi et al, "The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria," Infection and Immunity, vol. 76, No. 8, pp. 3817-3823 (Aug. 2008).

Roden et al, "Positively Charged Termini of the L2 Minor Capsid Protein Are Necessary for Papillomavirus Infection," Journal of Virology, vol. 75, No. 21, pp. 10493-10497 (Nov. 2001).

Rosa-Calatrava et al, "Functional Analysis of Adenovirus Protein IX Identifies Domains Involved in Capsid Stability, Transcriptional Activity, and Nuclear Reorganization," Journal of Virology, vol. 75, No. 15, pp. 7131-7141 (Aug. 2001).

Schiller et al, "Understanding and learning from the success of prophylactic human papillomavirus vaccines," Nature Reviews Microbiology, vol. 10, pp. 681-692 (Oct. 2012).

Schiller et al, "A Review of Clinical Trials of Human Papillomavirus Prophylactic Vaccines," Vaccine, vol. 30, Supplement, pp. F123-F138 (2012).

Smith et al, "Human papillomavirus type distribution in invasive cervical cancer and high-grade cervical lesions: A meta-analysis update," International Journal of Cancer, vol. 121, No. 3, pp. 621-632 (2007).

Vellinga et al, "Spacers Increase the Accessibility of Peptide Ligands Linked to the Carboxyl Terminus of Adenovirus Minor Capsid Protein IX," Journal of Virology, vol. 78, No. 7, pp. 3470-3479 (Apr. 2004).

Vogels et al, "Replication-Deficient Human Adenovirus Type 35 Vectors for Gene Transfer and Vaccination: Efficient Human Cell Infection and Bypass of Preexisting Adenovirus Immunity," Journal of Virology, vol. 77, No. 15, pp. 8263-8271 (Aug. 2003).

Vogels et al, "High-level expression from two independent expression cassettes in replication-incompetent adenovirus type 35 vector," Journal of General Virology, vol. 88, pp. 2915-2924 (2007).

Int'l Search Report and Written Opinion dated Oct. 6, 2017 in Int'l Application No. PCT/EP2017/067383.

Gambhira et al, "A Protective and Broadly Cross-Neutralizing Epitope of Human Papillomavirus L2," Journal of Virology, vol. 81, No. 24, pp. 13927-13931 (Dec. 1, 2007).

Jagu et al, "Concatenated Multitype L2 Fusion Proteins as Candidate Prophylactic Pan-Human Papillomavirus Vaccines," Journal of the National Cancer Institute, vol. 101, No. 11, pp. 782-792 (Jun. 2, 2009).

Jagu et al, "Optimization of Multimeric Human Papillomavirus L2 Vaccines," PLOS One, vol. 8, No. 1, p. e55538 (Jan. 31, 2013).

Wu et al, "Capsid display of a conserved human papillomavirus L2 peptide in the adenovirus 5 hexon protein: a candidate prophylactic hpv vaccine approach," Virology Journal, vol. 321, No. 2, pp. 205-215 (Sep. 11, 2015).

Gu et al, "Adenoviral vectors elicit humoral immunity against variable loop 2 of clade C HIV-1 gp120 via 'Antigen Capsid-Incorporation' strategy," Virology, vol. 487, pp. 75-84 (Oct. 23, 2015).

Jagu et al, "Durable immunity to oncogenic human papillomaviruses elicited by adjuvanted recombinant Adeno-associated virus-like particle immunogen displaying L2 17-36 epitopes," Vaccine, vol. 33, No. 42, pp. 5553-5563 (Sep. 15, 2015).

(56) References Cited

OTHER PUBLICATIONS

Tyler et al, "Immunization with a consensus epitope from human papillomavirus L2 induces antibodies that are broadly neutralizing," Vaccine, vol. 32, No. 34, pp. 4267-4274 (Jun. 21, 2014).

* cited by examiner

//www.hanna seitz

SEQUENCE LISTING

```
<160> NUMBER OF SEQ ID NOS: 16

<210> SEQ ID NO 1
<211> LENGTH: 90
<212> TYPE: PRT
<213> ORGANISM: Artificial Sequence
<220> FEATURE:
<223> OTHER INFORMATION: Sx3 HPV 45.18.16
```

<400> SEQUENCE: 1

Lys Arg Ala Ser Ala Thr Asp Leu Tyr Arg Thr Cys Lys Gln Ser Gly
1               5                   10                  15

Thr Cys Pro Pro Asp Val Ile Asn Lys Val Glu Gly Thr Thr Lys Arg
            20                  25                  30

Ala Ser Val Thr Asp Leu Tyr Lys Thr Cys Lys Gln Ser Gly Thr Cys
        35                  40                  45

Pro Pro Asp Val Val Pro Lys Val Glu Gly Thr Thr Lys Arg Ala Ser
    50                  55                  60

Ala Thr Gln Leu Tyr Lys Thr Cys Lys Gln Ala Gly Thr Cys Pro Pro
65                  70                  75                  80

Asp Ile Ile Pro Lys Val Glu Gly Lys Thr
                85                  90

<210> SEQ ID NO 2
<211> LENGTH: 120
<212> TYPE: PRT
<213> ORGANISM: Artificial Sequence
<220> FEATURE:
<223> OTHER INFORMATION: Sx4 HPV 31.45.18.16

<400> SEQUENCE: 2

Lys Arg Ala Ser Ala Thr Gln Leu Tyr Gln Thr Cys Lys Ala Ala Gly
1               5                   10                  15

Thr Cys Pro Ser Asp Val Ile Pro Lys Ile Glu His Thr Thr Lys Arg
            20                  25                  30

Ala Ser Ala Thr Asp Leu Tyr Arg Thr Cys Lys Gln Ser Gly Thr Cys
        35                  40                  45

Pro Pro Asp Val Ile Asn Lys Val Glu Gly Thr Thr Lys Arg Ala Ser
    50                  55                  60

Val Thr Asp Leu Tyr Lys Thr Cys Lys Gln Ser Gly Thr Cys Pro Pro
65                  70                  75                  80

Asp Val Val Pro Lys Val Glu Gly Thr Thr Lys Arg Ala Ser Ala Thr
                85                  90                  95

Gln Leu Tyr Lys Thr Cys Lys Gln Ala Gly Thr Cys Pro Pro Asp Ile
            100                 105                 110

Ile Pro Lys Val Glu Gly Lys Thr
        115                 120

<210> SEQ ID NO 3
<211> LENGTH: 120
<212> TYPE: PRT
<213> ORGANISM: Artificial Sequence
<220> FEATURE:
<223> OTHER INFORMATION: Sx4 HPV 33.45.18.16

<400> SEQUENCE: 3

Lys Arg Ala Ser Ala Thr Gln Leu Tyr Gln Thr Cys Lys Ala Thr Gly
1               5                   10                  15

Thr Cys Pro Pro Asp Val Ile Pro Lys Val Glu Gly Ser Thr Lys Arg
            20                  25                  30

Ala Ser Ala Thr Asp Leu Tyr Arg Thr Cys Lys Gln Ser Gly Thr Cys
        35                  40                  45

Pro Pro Asp Val Ile Asn Lys Val Glu Gly Thr Thr Lys Arg Ala Ser
    50                  55                  60

Val Thr Asp Leu Tyr Lys Thr Cys Lys Gln Ser Gly Thr Cys Pro Pro
65                  70                  75                  80

Asp Val Val Pro Lys Val Glu Gly Thr Thr Lys Arg Ala Ser Ala Thr
            85                  90                  95

Gln Leu Tyr Lys Thr Cys Lys Gln Ala Gly Thr Cys Pro Pro Asp Ile
            100                 105                 110

Ile Pro Lys Val Glu Gly Lys Thr
            115                 120

<210> SEQ ID NO 4
<211> LENGTH: 150
<212> TYPE: PRT
<213> ORGANISM: Artificial Sequence
<220> FEATURE:
<223> OTHER INFORMATION: Sx5 HPV 31.33.45.18.16

<400> SEQUENCE: 4

Lys Arg Ala Ser Ala Thr Gln Leu Tyr Gln Thr Cys Lys Ala Ala Gly
1               5                   10                  15

Thr Cys Pro Ser Asp Val Ile Pro Lys Ile Glu His Thr Thr Lys Arg
            20                  25                  30

Ala Ser Ala Thr Gln Leu Tyr Gln Thr Cys Lys Ala Thr Gly Thr Cys
            35                  40                  45

Pro Pro Asp Val Ile Pro Lys Val Glu Gly Ser Thr Lys Arg Ala Ser
50                  55                  60

Ala Thr Asp Leu Tyr Arg Thr Cys Lys Gln Ser Gly Thr Cys Pro Pro
65                  70                  75                  80

Asp Val Ile Asn Lys Val Glu Gly Thr Thr Lys Arg Ala Ser Val Thr
            85                  90                  95

Asp Leu Tyr Lys Thr Cys Lys Gln Ser Gly Thr Cys Pro Pro Asp Val
            100                 105                 110

Val Pro Lys Val Glu Gly Thr Thr Lys Arg Ala Ser Ala Thr Gln Leu
            115                 120                 125

Tyr Lys Thr Cys Lys Gln Ala Gly Thr Cys Pro Pro Asp Ile Ile Pro
            130                 135                 140

Lys Val Glu Gly Lys Thr
145                 150

<210> SEQ ID NO 5
<211> LENGTH: 150
<212> TYPE: PRT
<213> ORGANISM: Artificial Sequence
<220> FEATURE:
<223> OTHER INFORMATION: Sx5 HPV 52/58.31.45.18.16

<400> SEQUENCE: 5

Lys Arg Ala Ser Ala Thr Gln Leu Tyr Gln Thr Cys Lys Ala Ser Gly
1               5                   10                  15

Thr Cys Pro Pro Asp Val Ile Pro Lys Val Glu Gly Thr Thr Lys Arg
            20                  25                  30

Ala Ser Ala Thr Gln Leu Tyr Gln Thr Cys Lys Ala Ala Gly Thr Cys
            35                  40                  45

Pro Ser Asp Val Ile Pro Lys Ile Glu His Thr Thr Lys Arg Ala Ser
50                  55                  60

Ala Thr Asp Leu Tyr Arg Thr Cys Lys Gln Ser Gly Thr Cys Pro Pro
65                  70                  75                  80

Asp Val Ile Asn Lys Val Glu Gly Thr Thr Lys Arg Ala Ser Val Thr
            85                  90                  95

Asp Leu Tyr Lys Thr Cys Lys Gln Ser Gly Thr Cys Pro Pro Asp Val

```
            100                 105                 110

Val Pro Lys Val Glu Gly Thr Thr Lys Arg Ala Ser Ala Thr Gln Leu
        115                 120                 125

Tyr Lys Thr Cys Lys Gln Ala Gly Thr Cys Pro Pro Asp Ile Ile Pro
        130                 135                 140

Lys Val Glu Gly Lys Thr
145                 150

<210> SEQ ID NO 6
<211> LENGTH: 120
<212> TYPE: PRT
<213> ORGANISM: Artificial Sequence
<220> FEATURE:
<223> OTHER INFORMATION: Sx4 HPV 6.31.33.16

<400> SEQUENCE: 6

Lys Arg Ala Ser Ala Thr Gln Leu Tyr Gln Thr Cys Lys Leu Thr Gly
1               5                  10                  15

Thr Cys Pro Pro Asp Val Ile Pro Lys Val Glu His Asn Thr Lys Arg
            20                  25                  30

Ala Ser Ala Thr Gln Leu Tyr Gln Thr Cys Lys Ala Ala Gly Thr Cys
        35                  40                  45

Pro Ser Asp Val Ile Pro Lys Ile Glu His Thr Thr Lys Arg Ala Ser
    50                  55                  60

Ala Thr Gln Leu Tyr Gln Thr Cys Lys Ala Thr Gly Thr Cys Pro Pro
65                  70                  75                  80

Asp Val Ile Pro Lys Val Glu Gly Ser Thr Lys Arg Ala Ser Ala Thr
                85                  90                  95

Gln Leu Tyr Lys Thr Cys Lys Gln Ala Gly Thr Cys Pro Pro Asp Ile
                100                 105                 110

Ile Pro Lys Val Glu Gly Lys Thr
            115                 120

<210> SEQ ID NO 7
<211> LENGTH: 120
<212> TYPE: PRT
<213> ORGANISM: Artificial Sequence
<220> FEATURE:
<223> OTHER INFORMATION: Sx4 HPV 11.52/58.45.18

<400> SEQUENCE: 7

Lys Arg Ala Ser Ala Thr Gln Leu Tyr Gln Thr Cys Lys Ala Thr Gly
1               5                  10                  15

Thr Cys Pro Pro Asp Val Ile Pro Lys Val Glu His Thr Thr Lys Arg
            20                  25                  30

Ala Ser Ala Thr Gln Leu Tyr Gln Thr Cys Lys Ala Ser Gly Thr Cys
        35                  40                  45

Pro Pro Asp Val Ile Pro Lys Val Glu Gly Thr Thr Lys Arg Ala Ser
    50                  55                  60

Ala Thr Asp Leu Tyr Arg Thr Cys Lys Gln Ser Gly Thr Cys Pro Pro
65                  70                  75                  80

Asp Val Ile Asn Lys Val Glu Gly Thr Thr Lys Arg Ala Ser Val Thr
                85                  90                  95

Asp Leu Tyr Lys Thr Cys Lys Gln Ser Gly Thr Cys Pro Pro Asp Val
                100                 105                 110

Val Pro Lys Val Glu Gly Thr Thr
            115                 120
```

<210> SEQ ID NO 8
<211> LENGTH: 120
<212> TYPE: PRT
<213> ORGANISM: Artificial Sequence
<220> FEATURE:
<223> OTHER INFORMATION: Sx4 HPV 31.45.18.16

<400> SEQUENCE: 8

```
Lys Arg Ala Ser Ala Thr Gln Leu Tyr Gln Thr Cys Lys Ala Ala Gly
1               5                   10                  15

Thr Cys Pro Ser Asp Val Ile Pro Lys Ile Glu His Thr Thr Gly Thr
            20                  25                  30

Gly Ser Gly Ser Gly Gly Arg Thr Gly Tyr Val Pro Leu Gly Gly Arg
        35                  40                  45

Ser Asn Thr Val Val Asp Val Gly Pro Thr Arg Pro Asp Pro Ser Ile
    50                  55                  60

Val Thr Leu Ile Glu Asp Ser Ser Val Val Thr Ser Gly Ala Pro Arg
65                  70                  75                  80

Pro Thr Phe Thr Gly Thr Ser Gly Phe Asp Ser Asp Pro Ser Ile Val
                85                  90                  95

Ser Leu Val Glu Glu Thr Ser Phe Ile Asp Ala Gly Ala Pro Thr Ser
            100                 105                 110

Val Pro Ser Ile Pro Pro Asp Val
        115                 120
```

<210> SEQ ID NO 9
<211> LENGTH: 32
<212> TYPE: PRT
<213> ORGANISM: Artificial Sequence
<220> FEATURE:
<223> OTHER INFORMATION: Spacer 1

<400> SEQUENCE: 9

```
Cys Asn Gly Thr Asp Ala Lys Ile Lys Leu Ile Lys Gln Glu Leu Asp
1               5                   10                  15

Lys Tyr Lys Asn Ala Val Thr Glu Leu Gln Leu Leu Met Gln Ser Thr
            20                  25                  30
```

<210> SEQ ID NO 10
<211> LENGTH: 33
<212> TYPE: PRT
<213> ORGANISM: Artificial Sequence
<220> FEATURE:
<223> OTHER INFORMATION: Spacer 2

<400> SEQUENCE: 10

```
Thr Asn Glu Lys Phe His Gln Ile Glu Lys Glu Phe Ser Glu Val Glu
1               5                   10                  15

Gly Arg Ile Gln Asp Leu Glu Lys Tyr Val Glu Asp Thr Lys Ile Asp
            20                  25                  30

Leu
```

<210> SEQ ID NO 11
<211> LENGTH: 30
<212> TYPE: PRT
<213> ORGANISM: Artificial Sequence
<220> FEATURE:
<223> OTHER INFORMATION: Spacer 3

<400> SEQUENCE: 11

```
Gln Thr Asn Ala Arg Ala Ile Ala Ala Met Lys Asn Ser Ile Gln Ala
```

```
1               5                   10                  15
Thr Asn Arg Ala Ile Phe Glu Val Lys Glu Gly Thr Gln Gln
            20                  25                  30
```

<210> SEQ ID NO 12
<211> LENGTH: 139
<212> TYPE: PRT
<213> ORGANISM: Artificial Sequence
<220> FEATURE:
<223> OTHER INFORMATION: HAdV-35 pIX

<400> SEQUENCE: 12

```
Met Ser Gly Asn Ala Ser Phe Lys Gly Gly Val Phe Ser Pro Tyr Leu
1               5                   10                  15

Thr Gly Arg Leu Pro Ser Trp Ala Gly Val Arg Gln Asn Val Met Gly
            20                  25                  30

Ser Thr Val Asp Gly Arg Pro Val Gln Pro Ala Asn Ser Ser Thr Leu
        35                  40                  45

Thr Tyr Ala Thr Leu Ser Ser Pro Leu Asp Ala Ala Ala Ala
    50                  55                  60

Ala Ala Ala Ser Val Ala Ala Asn Thr Val Leu Gly Met Gly Tyr Tyr
65                  70                  75                  80

Gly Ser Ile Val Ala Asn Ser Thr Ser Ser Asn Asn Pro Ser Thr Leu
                85                  90                  95

Thr Gln Asp Lys Leu Leu Val Leu Leu Ala Gln Leu Glu Ala Leu Thr
            100                 105                 110

Gln Arg Leu Gly Glu Leu Ser Gln Gln Val Ala Glu Leu Arg Val Gln
        115                 120                 125

Thr Glu Ser Ala Val Gly Thr Ala Lys Ser Lys
    130                 135
```

<210> SEQ ID NO 13
<211> LENGTH: 134
<212> TYPE: PRT
<213> ORGANISM: Artificial Sequence
<220> FEATURE:
<223> OTHER INFORMATION: HAdV-26 pIX

<400> SEQUENCE: 13

```
Met Asn Gly Thr Gly Gly Ala Phe Glu Gly Gly Leu Phe Ser Pro Tyr
1               5                   10                  15

Leu Thr Thr Arg Leu Pro Gly Trp Ala Gly Val Arg Gln Asn Val Met
            20                  25                  30

Gly Ser Thr Val Asp Gly Arg Pro Val Leu Pro Ala Asn Ser Ser Thr
        35                  40                  45

Met Thr Tyr Ala Thr Val Gly Asn Ser Ser Leu Asp Ser Thr Ala Ala
    50                  55                  60

Ala Ala Ala Ala Ala Ala Met Thr Ala Thr Arg Leu Ala Ser Ser
65                  70                  75                  80

Tyr Met Pro Ser Ser Gly Ser Ser Pro Ser Val Pro Ser Ser Ile Ile
                85                  90                  95

Ala Glu Glu Lys Leu Leu Ala Leu Leu Ala Glu Leu Glu Ala Leu Ser
            100                 105                 110

Arg Gln Leu Ala Ala Leu Thr Gln Gln Val Ser Glu Leu Arg Glu Gln
        115                 120                 125

Gln Gln Gln Gln Asn Lys
    130
```

```
<210> SEQ ID NO 14
<211> LENGTH: 14
<212> TYPE: PRT
<213> ORGANISM: Artificial Sequence
<220> FEATURE:
<223> OTHER INFORMATION: epitope 1

<400> SEQUENCE: 14

Gln Leu Tyr Thr Cys Lys Gln Ala Gly Thr Cys Pro Pro Asp
1               5                   10

<210> SEQ ID NO 15
<211> LENGTH: 13
<212> TYPE: PRT
<213> ORGANISM: Artificial Sequence
<220> FEATURE:
<223> OTHER INFORMATION: epitope 2

<400> SEQUENCE: 15

Arg Thr Gly Tyr Ile Pro Leu Gly Thr Arg Pro Pro Thr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: epitope 3

<400> SEQUENCE: 16

Leu Val Glu Glu Thr Ser Phe Ile Asp Ala Gly Ala Pro
1               5                   10
```

HPV VACCINES

CROSS-REFERENCE TO RELATED APPLICATION

This application is a Section 371 of International Application No. PCT/EP2017/067383, filed Jul. 11, 2017, which was published in the English language on Jan. 18, 2018 under International Publication No. WO 2018/011196 A1, and claims priority under 35 U.S.C. § 119(b) to European Application No. 16179394.8, filed Jul. 14, 2016, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688097_586US", creation date of Jan. 9, 2019, and having a size of 14.0 KB. The sequence listing submitted via EFS-Web is part of the specification and is herein incorporated by reference in its entirety.

FIELD OF THE INVENTION

The invention relates to the field of vaccines. More in particular, the invention relates to the use of a recombinantly produced capsid-display adenoviral vector displaying multiple antigenic fragments of an HPV L2 protein on its minor capsid protein IX, said vector being used as a carrier of an HPV antigenic determinant for the development of a vaccine against HPV infections.

BACKGROUND OF THE INVENTION

Human Papillomavirus (HPV) is known cause of cervical cancer in woman but it can also cause penile, anal, vulvar, vaginal and orophanryngial cancers (Forman et al. 2012, Vaccine). Two prophylactic L1 protein virus-like particles (VLPs) based vaccines have been shown to prevent infection with the high risk cancerogenic HPV 16 and 18 types (Schiller et al. 2012, Vaccine). One of these also provides protection against HPV 6 and 11 types (Schiller et al. 2012, Vaccine).

Although these vaccines are highly effective at preventing HPV 16 and 18 infections, which cause approximately 70% of the cervical cancer cases worldwide, 13 other HPV types are known to be cancerogenic as well. In descending order of importance, genotypes HPV 45, HPV 31, HPV 33, HPV 52, HPV 58, HPV 35, HPV 56, HPV 51, HPV 39, HPV 68, HPV 73 and HPV 82 cause the remaining 30% of the worldwide reported cervical cancer cases (Hanna Seitz, 2014)). To ensure protection against the less prevalent HPV types, a nine-valent L1 VLP based vaccine has been developed which in addition to the HPV 6, 11, 16 and 18, also aims at providing protection against the HPV types 31, 33, 45, 52 and 58 (Munoz et al., 2004; Smith et al., 2007). Despite the effective prevention against infections from the mentioned genotypes, L1 VLP based vaccines offer limited cross-protection and they are also very expensive to manufacture. This prevents their global implementation, in particular in the developing world where ~80% of the HPV cases occur (Parkin & Bray, 2006; Schiller & Lowy, 2012).

Hence, there is a need for immunogenic vaccines that are (cross-) protective against many HPV types.

Figure 1A:
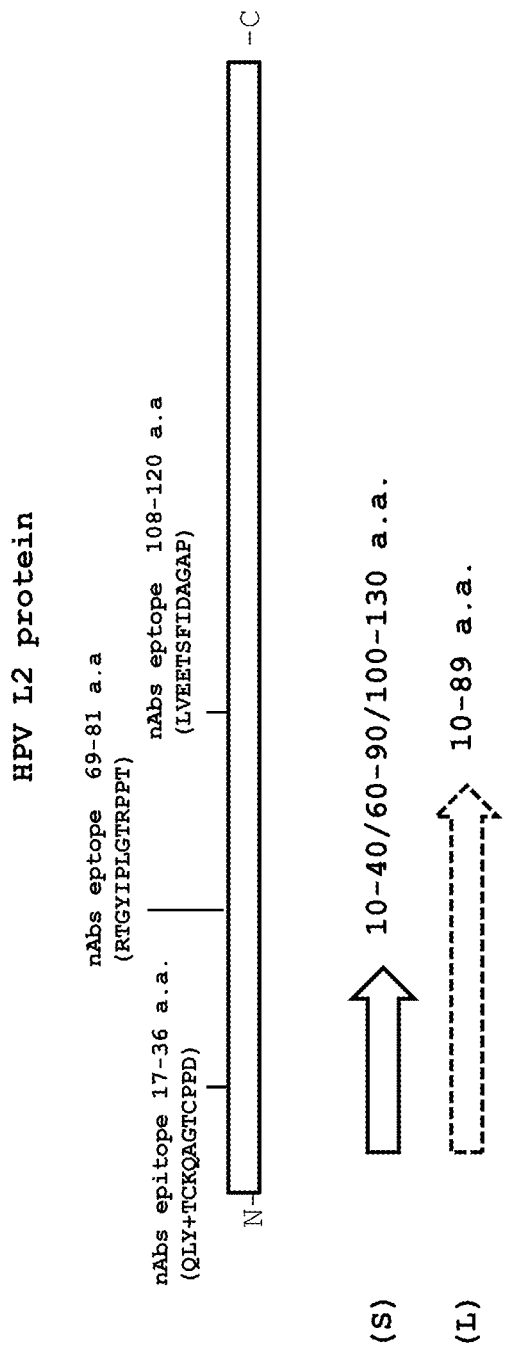
FIG. 1: L2 antigen and Vector design (A) Schematic drawing of the HPV L2 protein (N- and C-terminus) and its highly conserved linear QLY+TCKQAGTCPPD (+ is an amino acid that is variable amongst the human HPV types) 17-36 amino acids (a.a.) (SEQ ID NO:14), RTGYIPLG-TRPPT 69-81 a.a. (SEQ ID NO:15) and LVEETSFIDAGAP 108-120 a.a. (SEQ ID NO:16) neutralizing antibody (nAb) epitopes. Two distinct HPV L2 antigenic fragments, the (S)-design comprising the 10-40 a.a. (including the 17-36 a.a. nAb epitope) but also 60-90 a.a. and 100-130 a.a. (including the 69-81 a.a. or 108-120 a.a. nAb epitope) or the (L)-design comprising the 10-89 a.a. (including the 17-36 a.a. and the 69-81 a.a. nAb eptitopes) were genetically fused to protein IX, to generate pIX-L2 capsid display adenoviral vectors. (B) Human Adenovirus 35 (HAdV35) pIX-L2 capsid display vector with an 'empty' E1 cassette (CMV promoter and SV40 poly A signal) and the native protein IX promoter (P). Schematic drawing of the HAdV35 vectors genetically encoding, the (S) design 10-40 a.a. concatemer (i.e. repeat) of HPV type 16, 18 and 45 (Sx3), (Sx3)x3, the (L) design 10-89 a.a. concatemers (Lx3) or a combination of the (S) and (L) design (Sx2+L) fused to pIX via a 3 a.a. Glycine-linker (gly). (C) Human Adenovirus 26 (HAdV26) pIX-L2 capsid display vector with an 'empty' E1 cassette (CMV promoter and SV40 poly A signal) and the native protein IX promoter (P). Schematic drawing of the HAdV26 vectors genetically encoding the (S) design 10-40 a.a. HPV L2 protein concatemers of the different HPV types fused to protein IX via a 3 a.a. Glycine-linker (gly). The HAdV26 Sx3 vector contains the 10-40 a.a. of HPV types 16, 18 and 45, the Sx4 vector contains either HPV type 16, 18, 33 and 45 or 16, 18, 31 and 45, the Sx5 vector either the HPV type 16, 18, 31, 33 and 45 or 16, 18, 31, 45 and (52)58 and the Sx6 vector HPV type 16, 18, 31, 33, 45 and 52(58). The sequence of HPV type 52 and 58 is indentical in the 10-40 a.a. HPV L2 region. (D) Schematic drawing of HAdV35 pIX-L2 display vectors genetically encoding the (S) design 10-40 a.a. HPV L2 concatemers of four different HPV types 6, 16, 31, 33 or 11, 18, 45 and (52)58 fused to protein IX via a 3 a.a. Glycine-linker (gly). The two different Sx4 vectors either contain an 'empty' E1 cassette (CMV promoter and SV40 poly A signal) and the native protein IX promoter (P).
Figure 1B:
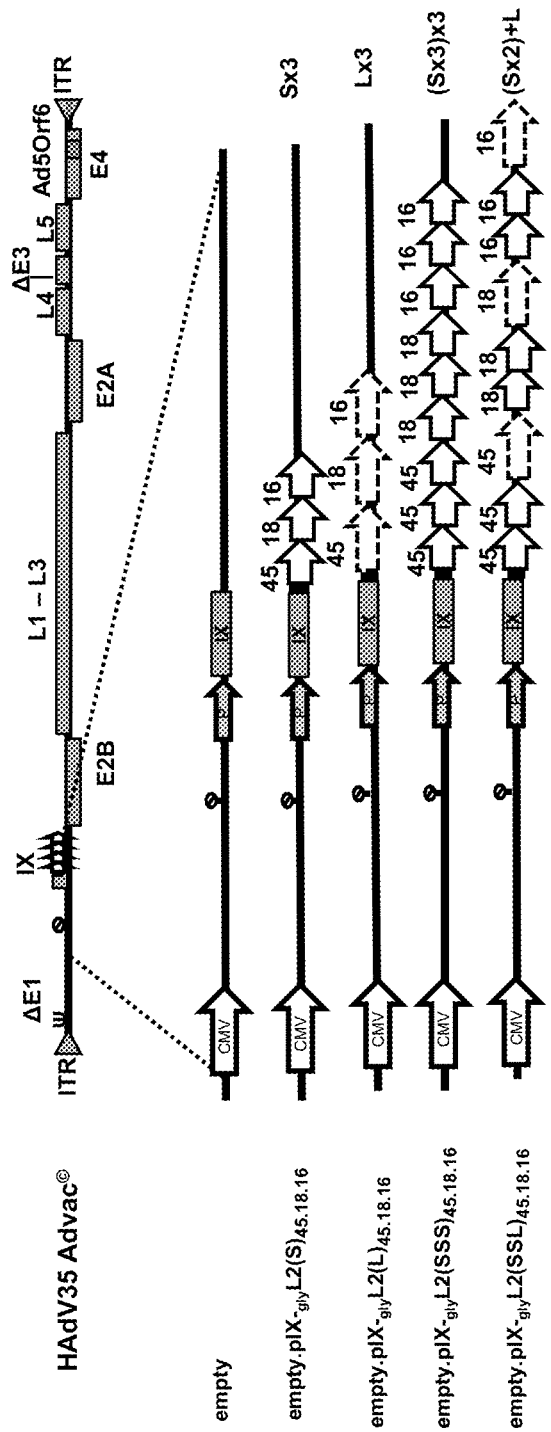

FIG. 3: Capsid incorporation of the HPV L2 (Sx4) designs. (A) pIX-Sx4 capsid incorporation was determined by Western blot. Levels of the pIX-Sx4 in purified vector preparations of HAdV35.Empty.pIX-L2(S)11.52/58.45.18 and HAdV35.Empty.pIX-L2(S)6.31.33.16 were compared to the levels of pIX-Sx3 in a purified preparation of HAdV35.Empty.pIX-L2(S)45.18.16. Three different concentrations: $1.5 \times 10^{10}$, $1 \times 10^{10}$ and $0.17 \times 10^{10}$ VP/well of the Sx4 and Sx3 pIX modified vectors were separated on gel, blotted and stained with anti-L2 serum (pIX-Sx3: 25 kDa, pIX-Sx4: 28 kDa) (HPV 16 positive mouse serum) and the loading control anti-fiber monoclonal antibody (HAdV5 fiber knob, 4D2, 35 kDa). The HAdV35.Empty was used as the non-modified pIX L2 negative control. (B) pIX-Sx4 (mix) HPV epitopes capsid incorporation was determined by Western blot. Levels of the pIX-Sx4-mix in purified vector preparation of HAdV26.Empty.pIX-L2(Sx4.mix)31, 45.18.16 was compared to HAdV26.Empty.pIX-L2(S)33.45.18.16 and pIX-Sx3 in a purified preparation of HAdV26.Empty.pIX-L2(S)45.18.16. Three different concentrations: $1.5 \times 10^{10}$, $1 \times 10^{10}$ and $0.17 \times 10^{10}$ VP/well of the Sx4 and Sx3 pIX modified vectors were separated on gel, blotted and stained with anti-L2 serum (pIX-Sx3: 25 kDa, pIX-Sx4: 28 kDa) (HPV 16 positive mouse serum) and the loading control anti-fiber monoclonal antibody (HAdV5 fiber knob, 4D2, 35 kDa). The HAdV26.Empty was used as the non-modified pIX L2 negative control.

FIG. 4: Humoral responses against the HAdV35 pIX-L2(S)45.18.16 (Sx3) pIX-L2(S)6.31.33.16 and pIX-L2(S)11.52/58.45.18 (Sx4) vectors in mice (A) Schematic representation of the immunization schedule. Four groups of eight CB6F1 mice (n=8) were primed with $1 \times 10^{10}$ VP of respectively HAdV35.Empty.pIX-L2(S)45.18.16, HAdV35.Empty.pIX-L2(S)6.31.33.16, HAdV35.Empty.pIX-L2(S)11.52/58.45.18 or a mix of HAdV35.Empty.pIX-L2(S)6.31.33.16 & HAdV35.Empty.pIX-L2(S)11.52/58.45.18. As a negative control HAdV35.Empty vector (n=3, $1 \times 10^{10}$ VP) was administered to a fifth group. Eight weeks later the mice were boosted with the same vectors (at the same concentration) as administered during the prime immunization. Four weeks after the boost immunization mice were sacrificed (week 12). The serum of the mice was collected at two week interval (*) for HPV type specific antibody response analysis in the HPV MSD ELISA. (B) Antibody responses in serum at week 8 and week 12 against 9 different HPV types (6, 11, 16, 18, 31, 33, 45, 52/58 and 59) as measured by MSD ELISA. The HPV type specific responses induced by each vector or vector mix are plotted in the graph ($log_{10}$). The dotted line indicates the lowest and highest $log_{10}$ ELISA titers. Bonferroni correction and tests were performed at the 5% significance level (<0.05). (C) HPV 16, 18, 31 and 59 in vitro pseudovirions virus (PsV) neturalization assay (VNA) displayed in Luminescence $Log_{10}$ expression. Serum of mice immunized with $1 \times 10^{10}$ VP/mouse HAdV35 pIX-L2 (Sx3), pIX-L2(Sx4)16, pIX-L2(Sx4)18 and a mix of pIX-L2(Sx4)16 & pIX-L2(Sx4)18 were analyzed in in vitro PsV Virus Neutralization assays. As a positive neutralization control for HPV 16 and 18, serum of quadrivalent Gardasil (HPV 6, 11, 16, 18) immunized mice are taken along. As a luminescence postivie control the respective HPV pseudovirions are taken along. Horizontal line indicates the group average. The dotted lines in each graph depict the average of the PsVs without Furine. P-values were adjusted using a 3-fold Bonferroni correction and tests were performed at the 5% significance level (<0.05).

FIG. 5: Genetic stability of pIX-L2 display vectors in PER.C6® cells (A) A schematic representation of small scale genetic stability testing by PCR analysis of the viral DNA after extended passaging in PER.C6® cells. Viral passage number (VPN) 14 is representative of 4 passages beyond the envisioned commercial scale process. Batches or plaques are up-scaled/passaged in adherent PER.C6® cells (adPER.C6® cells) up to approximately 7 VPN. The passaging is then continued with an additional 7 VPN in suspension PER.C6® cells (sPER.C6® cells) under controlled conditions by infecting $1 \times 10^6$ viable cells per ml (vc/ml) with either 35 (HAdV35) or 900 (HAdV26) VP/cell. The VP titers were determined by a viral particle quantitative PCR (VP-QPCR) on crude material prior to infection at each VPN. Viral DNA is isolated and a pIX-PCR is performed with primers flanking the pIX-modified region in the HAdV genome and confirmed by sequencing. (B) An agarose gel analysis of pIX-PCR of five plaques (1-5) each of HAdV35.Empty.pIX-L2(S)11.52/58.45.18 and HAdV35.Empty.pIX-L2(S)6.31.33.16 vectors at VPN 14. The + refers to the positive plasmid control (942 bp), (−) refers to the non-modified pIX plasmid control (570 bp) and $H_2O$ refers to the PCR water control. The M stands for the molecular weight markers. Asterisks indicate non-specific bands detected in the pIX-PCR.

DESCRIPTION OF THE INVENTION

The present invention relates to a recombinant adenoviral vector comprising a capsid protein IX fused to an antigen wherein said antigen comprises 3 to 5 consecutive amino acid motifs, wherein each motif is about 20 to about 40 amino acids long and wherein each motif comprises an antigenic fragment of a HPV L2 protein from a different HPV type. Preferably at least one of said motifs comprises an antigenic fragment which comprises amino acid residues 17-36 of a HPV L2 protein. The HPV L2 protein can be from any HPV type. More preferably said HPV L2 protein type is selected from the group consisting of HPV types 6, 11, 16, 18, 31, 33, 35, 39, 45, 52, 56, 58, 68, 73 and 82.

In a preferred embodiment of the present invention, said antigen comprises 3 consecutive amino acid motifs which have a length between about 20 and about 40 amino acids and which comprise the amino acid residues 17-36 of a HPV L2 protein of the HPV types 45, 18 and 16, respectively. Preferably, said antigen comprises SEQ ID NO:1.

In a more preferred embodiment, said antigen comprises 4 consecutive amino acid motifs which have a length between about 20 and about 40 amino acids, and which comprise the amino acid residues 17-36 of a HPV L2 protein of the HPV types 31, 45, 18 and 16 respectively; 33, 45, 18 and 16 respectively; 6, 31, 33 and 16 respectively or 11, 52/58, 45 and 18 respectively (the L2 protein of HPV types 52 and 58 are identical in the selected 10-40 amino acids). Preferably, said antigens comprise SEQ ID NO:2, SEQ ID NO:3, SEQ ID NO:6 or SEQ ID NO:7, respectively. In another preferred embodiment of the present invention, said antigen comprises 5 consecutive amino acid motifs which have a length between about 20 and about 40 amino acids, and which comprise the 17-36 amino acid residues of a HPV L2 protein of the HPV types 33, 31, 45, 18 and 16 respectively or 52, 31, 45, 18 and 16 respectively. Preferably, said antigen comprises SEQ ID NO:4 or SEQ ID NO:5, respectively.

Preferably said amino acid motifs comprise about 30 amino acid residues. In a preferred embodiment of the present invention, each motif comprises the about 10 to about 40 amino acid residues of said HPV L2 proteins. In another embodiment of the present invention, one of the 3 to 5 amino acid motifs comprises the amino acid residues 69-81 of the HPV L2 protein or the amino acid residues 108-121 of the HPV L2 protein, instead of the amino acid residues 17-36. In another embodiment of the present invention, one of the 3 to 5 amino acid motifs comprises the amino acid residues 69-81 of the HPV L2 protein and one of the 3 to 5 amino acid motifs comprises the amino acid residues 108-121 of the HPV L2 protein, instead of the amino acid residues 17-36.

In another preferred embodiment of the present invention, said antigen comprises 4 consecutive amino acid motifs each having a length between about 20 and about 40 amino acids, said first motif comprising the amino acid residues 17-36 of a HPV L2 type 31 protein, said second motif comprising the amino acid residues 69-81 of a HPV L2 type 45 protein, said third motif comprising the amino acid residues 108-121 of a HPV L2 type 18 protein, and said fourth motif comprising the amino acid residues 108-121 of a HPV L2 type 16 protein, respectively. Preferably said amino acid motifs comprise about 30 amino acid residues. More preferably, said antigen comprises SEQ ID NO:8.

In a preferred embodiment of the present invention, the pIX protein and the antigen are linked together by a linker or a spacer. In another preferred embodiment, the linker comprises an amino acid sequence having 2 to 15 consecutive flexible residues of glycine and/or serine. In a more preferred embodiment, the linker comprises an amino acid sequence having 3 consecutive flexible residues of glycine (GGG). In yet another preferred embodiment, the spacer comprises the amino acid sequence of SEQ ID NO:9, SEQ ID NO:10 or SEQ ID NO:11.

In a more preferred embodiment of the present invention, said adenoviral vector is selected from the group consisting of: HAdV4, HAdV11, HAdV26, HAdV35, HAdV48, HAdV49, HAdV50, non-human primate vectors and chimeric vectors. Preferably, the recombinant adenoviral vector is a HAdV26 or HAdV35.

In another preferred embodiment, the recombinant adenoviral vector according to the present invention further comprises a nucleic acid encoding one or more heterologous proteins as a transgene. Preferably said nucleic acid is located in the E1 region of the adenovirus.

Another aspect of the present invention relates to a composition comprising a combination of at least two different recombinant adenoviral vectors according to the present invention. In a preferred embodiment, said composition comprises a first recombinant adenoviral vector, wherein the antigen comprises SEQ ID NO:6 and a second recombinant adenoviral vector, wherein the antigen comprises SEQ ID NO:7.

Another aspect of the present invention relates to a vaccine comprising a recombinant adenoviral vector or a composition according to the present invention, further comprising a pharmaceutically acceptable excipient.

Furthermore, the invention relates to the use of a vaccine according to the invention in the therapeutic, prophylactic or diagnostic treatment of HPV. The invention also relates to a method of inducing an immune response in a subject, comprising administering an adenoviral vector or vaccine as described herein.

DETAILED DESCRIPTION OF THE INVENTION

The present invention relates to a recombinant adenoviral vector comprising a capsid protein IX (pIX) fused to an antigen wherein said antigen comprises 3 to 5 consecutive amino acid motifs, wherein each motif is about 20 to about 40 amino acids long and wherein each motif comprises an antigenic fragment of a HPV L2 protein from a different HPV type. Preferably at least one of said motifs comprises an antigenic fragment which comprises amino acid residues 17-36 of a HPV L2 protein.

In certain embodiments, the antigen comprises 3, 4, or 5 consecutive amino acid motifs. The amino acid motifs may have a length of 19, 20, 21, 22, 23, 24, 25, 26, 27, 28, 29, 30, 31, 32, 33, 34, 35, 36, 37, 38, 39, 40 or 41 amino acids. The term "motif" as used herein means a short cluster of amino acids which shares structural and usually functional similarities. The amino acid motifs as defined for the present invention are amino acid portions from a HPV L2 protein, which comprise antigenic (amino acid) fragments of a HPV L2 protein, such as for example, but not limited to, the amino acid residues 17-36, the amino acid residues 69-81 and the amino acid residues 108-121 of a HPV L2 protein.

The term 'recombinant', as used herein means that it has been modified by the hand of man, e.g. it has altered terminal ends cloned therein and/or it comprises a heterologous gene, i.e. it is not a naturally occurring wild type adenovirus. Heterologous gene means that it is not naturally occurring on the adenovirus, i.e. it is not an adenoviral gene.

The recombinant adenoviral vector according to the present invention, is an adenoviral vector that comprises an adenoviral capsid protein IX that is fused to an antigen (or polypeptide) as defined previously. The antigen is therewith displayed at the surface of the adenoviral vector, onto the minor capsid protein IX. The antigen is fused to the C-terminus of the minor capsid protein IX. The fusion of pIX with the antigen is performed by genetically fusing the two genes in the adenoviral genome using well established molecular techniques.

The term Protein IX (pIX) refers to a minor capsid protein with the main function of stabilizing the icosahedral Adenovirus capsid (Rosa-Calatrava, Grave, Puvion-Dutilleul, Chatton, & Kedinger, 2001).

The pIX is adenovirus type specific, each adenovirus type has a different capsid pIX, i.e. the pIX in Adenovirus 35 (HAdV35) comprises the amino acid sequence SEQ ID NO:12; while the pIX in Adenovirus 26 (HAdV26) comprises the amino acid sequence SEQ ID NO:13.

An "adenovirus capsid protein" refers to a protein on the capsid of an adenovirus that is involved in determining the serotype and/or tropism of a particular adenovirus. Adenoviral capsid proteins typically include the fiber, penton and/or hexon proteins. An adenovirus of (or 'based upon') a certain serotype according to the invention typically comprises fiber, penton and/or hexon proteins of that certain serotype, and preferably comprises fiber, penton and hexon protein of that certain serotype. These proteins are typically encoded by the genome of the recombinant adenovirus. A recombinant adenovirus of a certain serotype may optionally comprise and/or encode other proteins from other adenovirus serotypes. Thus, as non-limiting example, a recombinant adenovirus that comprises hexon, penton and fiber of HAdV35 is considered a recombinant adenovirus based upon HAdV35.

The HPV minor L2 protein is a late protein involved in capsid formation. The L2 protein is required for HPV infection. It binds to the viral receptor with its highly conserved N-terminal region (Roden et al., 2001). Immunization with the L2 N-terminal peptides has shown to induce (cross-) protective neutralizing antibodies in different animal models (Karanam, Jagu, Huh, & Roden, 2009). The observed protection after immunization with the L2 N-terminal (poly-) peptides is mainly due to the highly conserved neutralizing and possibly binding epitopes identified in this region. The identified L2 neutralizing antibody (nAbs) epitopes in the N-terminal region include the highly conserved a.a. residues 17-36, a.a. residues 69-81 and a.a. residues 108-120 (Karanam et al., 2009).

In accordance with the present invention, the HPV minor L2 protein can be from any HPV type. The L2 protein is preferably selected from the group consisting of HPV type 6, 11, 16, 18, 45, 31, 33, 35, 52, 58, 35, 56, 51, 39, 68, 73 or 82 genotypes.

In a preferred embodiment of the present invention, the antigen fused to the pIX comprises 3 consecutive amino acid motifs which have a length between about 20 and about 40 amino acids, and which comprise the amino acid residues 17-36 of a HPV L2 protein of the HPV types 45, 18 and 16, respectively. Preferably, said antigenic fragment comprises SEQ ID NO:1.

In a more preferred embodiment, said antigen comprises 4 consecutive amino acid motifs which have a length between about 20 and about 40 amino acids, and which comprise the amino acid residues 17-36 of a HPV L2 protein of the HPV types 31, 45, 18 and 16 respectively; 33, 45, 18 and 16 respectively; 6, 31, 33 and 16 respectively or 11, 52/58, 45 and 18 respectively. Preferably, said antigens comprise SEQ ID NO:2, SEQ ID NO:3, SEQ ID NO:6 or SEQ ID NO:7, respectively.

In another preferred embodiment of the present invention, said antigen comprises 5 consecutive amino acid motifs which have a length between about 20 and about 40 amino acids, and which comprise the 17-36 amino acid residues of a HPV L2 protein of the HPV types 33, 31, 45, 18 and 16 respectively or 52, 31, 45, 18 and 16 respectively. Preferably, said antigen comprises SEQ ID NO:4 or SEQ ID NO:5, respectively.

Preferably said amino acid motifs comprise about 30 amino acid residues. In a preferred embodiment of the present invention, each motif comprises the about 10 to about 40 amino acid residues of said HPV L2 proteins. In another embodiment of the present invention, one of the 3 to 5 amino acid motifs comprises the amino acid residues 69-81 of the HPV L2 protein or the amino acid residues 108-121 of the HPV L2 protein, instead of the amino acid residues 17-36. In another embodiment of the present invention, one of the 3 to 5 amino acid motifs comprises the amino acid residues 69-81 of the HPV L2 protein and one of the 3 to 5 amino acid motifs comprises the amino acid residues 108-121 of the HPV L2 protein, instead of the amino acid residues 17-36.

In another preferred embodiment of the present invention, said antigen comprises 4 consecutive amino acid motifs each having a length between about 20 and about 40 amino acids, said first motif comprising the amino acid residues 17-36 of a HPV L2 type 31 protein, said second motif comprising the amino acid residues 69-81 of a HPV L2 type 45 protein, said third motif comprising the amino acid residues 108-121 of a HPV L2 type 18 protein, and said fourth motif comprising the amino acid residues 108-121 of a HPV L2 type 16 protein, respectively. Preferably said amino acid motifs comprise about 30 amino acid residues. More preferably, said antigen comprises SEQ ID NO:8.

The term "linker" and "spacer" refer to short peptide sequences that can be placed between protein domains, for instance between the antigen and the pIX. Linkers are composed of flexible residues such as glycine (gly) and/or serine in different size ranges, ensuring free movement of different domains relative to one another. Examples of linkers include but are not limited to 3-Gly (Gly-Gly-Gly) and middle linker (Gly-Gly-Ser-Gly)x2. In one preferred embodiment according to the present invention, the Glycine linker comprises an amino acid sequence having 2 to 15 consecutive glycine and/or Serine residues. In a preferred embodiment, the linker comprises an amino acid sequence having 3 consecutive flexible residues of glycine.

Several spacers could be used as well in the present invention, i.e. the ApoE4 protein alpha-helical 45 Å spacer (Vellinga et al., 2004) that is from human ApoE4 protein origin; the spacer 1 (SP1), a RSV Fusion protein; the spacer 2 (SP2), an Influenza A HA; the spacer 3 (SP3), a Mumps Fusion protein. The SP1-SP3 spacers are from viral origin and comprise the amino sequences SEQ ID NO: 9, SEQ ID NO: 10, SEQ ID NO: 11 respectively.

A recombinant adenovirus is 'based upon' an adenovirus as used herein, by derivation from the wild type, at least in sequence. This can be accomplished by molecular cloning, using the wild type genome or parts thereof as starting material. It is also possible to use the known sequence of a wild type adenovirus genome to generate (parts of) the genome de novo by DNA synthesis, which can be performed using routine procedures by service companies having business in the field of DNA synthesis and/or molecular cloning (e.g. GeneArt, Invitrogen, GenScripts, Eurofins).

The recombinant adenovirus of the present invention is preferably based upon an adenovirus from a serotype selected from the group consisting of: HAdV4, HAdV5, HAdV11, HAdV26, HAdV35, HAdV48, HAdV49 and Ad50. Preferably, said serotype is selected from the group of HAdV4, HAdV26, HAdV35, HAdV48, HAdV49 and HAdV50. Other possible types of adenoviruses suited for the present invention are included but not limited to: canine adenoviruses, chimp adenoviruses, gorilla adenoviruses and chimeric adenoviruses. More preferably, the recombinant adenoviral vector according to the present invention is a HAdV26 or HAdV35.

Another aspect of the present invention relates to a composition comprising a combination of at least two different recombinant adenoviral vectors according to the present invention. In a preferred embodiment, said composition comprises a first recombinant adenoviral vector, wherein the antigen comprises SEQ ID NO:6 and a second recombinant adenoviral vector, wherein the antigen comprises SEQ ID NO:7. Both adenoviral vectors can be either from the same serotype or from different serotypes. Preferably the recombinant adenoviral vectors are both based upon an adenovirus from serotype HAdV26 or HAdV35.

In a more preferred embodiment, the composition comprises a combination of at least two different recombinant HAdV35 adenoviral vectors, wherein a first recombinant adenoviral vector comprises an antigenic fragment comprising SEQ ID NO:6 and wherein a second recombinant adenoviral vector comprises an antigenic fragment comprising SEQ ID NO:7.

In another preferred embodiment, the composition comprises a combination of at least two different recombinant HAdV26 adenoviral vectors, wherein a first recombinant adenoviral vector comprises an antigen comprising SEQ ID NO:6 and wherein a second recombinant adenoviral vector comprises an antigen comprising SEQ ID NO:7. Sequences herein are provided from 5' to 3' direction, as custom in the art.

The replication-defective recombinant adenoviral vectors according to the present invention can further comprise a heterologous nucleic acid encoding a heterologous antigen (or polypeptide).

It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

In one particular aspect of the invention the recombinant viral vector according to the invention, comprises a nucleic acid encoding an antigenic determinant, or an immunogenic part thereof. Preferably, said heterologous nucleic acid is codon-optimized for elevated expression in a mammal, preferably a human. Codon-optimization is based on the required amino acid content, the general optimal codon usage in the mammal of interest and a number of provisions of aspects that should be avoided to ensure proper expression. Such aspects may be splice donor or—acceptor sites, stop codons, Chi-sites, poly(A) stretches, GC- and AT-rich sequences, internal TATA boxes, etcetera.

In a preferred embodiment, the invention relates to a replication-defective recombinant viral vector according to the invention, wherein the adenine plus thymine content in said heterologous nucleic acid, as compared to the cytosine plus guanine content, is less than 87%, preferably less than 80%, more preferably less than 59% and most preferably equal to approximately 45%.

The person skilled in the art will also appreciate that changes can be made to a protein, e.g. by amino acid substitutions, deletions, additions, etc, e.g. using routine molecular biology procedures. Generally, conservative amino acid substitutions may be applied without loss of function or immunogenicity of a polypeptide. This can easily be checked according to routine procedures well known to the skilled person.

The vectors of the present invention are recombinant adenoviruses, also referred to as recombinant adenoviral vectors. The preparation of recombinant adenoviral vectors is well known in the art.

In certain embodiments, an adenoviral vector according to the invention is deficient in at least one essential gene function of the E1 region, e.g. the E1a region and/or the E1b region, of the adenoviral genome that is required for viral replication. In certain embodiments, an adenoviral vector according to the invention is deficient in at least part of the non-essential E3 region. In certain embodiments, the vector is deficient in at least one essential gene function of the E1 region and at least part of the non-essential E3 region. The adenoviral vector can be "multiply deficient", meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region).

Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, 6,113,913, and 8,932,607 and Thomas Shenk, "Adenoviridae and their Replication", M. S. Horwitz, "Adenoviruses", Chapters 67 and 68, respectively, in Virology, B. N. Fields et al., eds., 3d ed., Raven Press, Ltd., New York (1996), and other references mentioned herein. Typically, construction of adenoviral vectors involves the use of standard molecular biological techniques, such as those described in, for example, Sambrook et al., Molecular Cloning, a Laboratory Manual, 2d ed., Cold Spring Harbor Press, Cold Spring Harbor, N.Y. (1989), Watson et al., Recombinant DNA, 2d ed., Scientific American Books (1992), and Ausubel et al., Current Protocols in Molecular Biology, Wiley Interscience Publishers, NY (1995), and other references mentioned herein.

According to the invention, the adenoviral vector is preferably selected from the group of HAdV4, HAdV11, HAdV26, HAdV35, HAdV48, HAdV49, HAdV50, non-human primate vectors and chimeric vectors. The adenoviral vectors according to the invention generally have low sero-prevalence and/or low pre-existing neutralizing antibody titers in the human population. Recombinant adenoviral vectors with different transgenes are evaluated in clinical trials, and thus far show to have an excellent safety profile. Preparation of HAdV26 vectors is described, for example, in WO 2007/104792 and in Abbink et al., (2007) Virol 81(9): 4654-63. Exemplary genome sequences of HAdV26 are found in GenBank Accession EF 153474 and in SEQ ID NO:1 of WO 2007/104792. Preparation of HAdV35 vectors is described, for example, in U.S. Pat. No. 7,270,811, in WO 00/70071, and in Vogels et al., (2003) J Virol 77(15): 8263-71. Exemplary genome sequences of HAdV35 are found in GenBank Accession AC_000019 and in FIG. 6 of WO 00/70071. A recombinant adenovirus according to the invention may be replication-competent or replication-deficient.

In certain embodiments, the adenovirus is replication deficient, e.g. because it contains a deletion in the E1 region of the genome. As known to the skilled person, in case of deletions of essential regions from the adenovirus genome, the functions encoded by these regions have to be provided in trans, preferably by the producer cell, i.e. when parts or whole of E1, E2 and/or E4 regions are deleted from the adenovirus, these have to be present in the producer cell, for instance integrated in the genome thereof, or in the form of so-called helper adenovirus or helper plasmids. The adenovirus may also have a deletion in the E3 region, which is dispensable for replication, and hence such a deletion does not have to be complemented.

A producer cell (sometimes also referred to in the art and herein as 'packaging cell' or 'complementing cell' or 'host cell') that can be used can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Any E1-complementing producer cell can be used, such as human retina cells immortalized by E1, e.g. 911 or PER.C6 cells (see U.S. Pat. No. 5,994,128), E1-transformed amniocytes (See EP patent 1230354), E1-transformed A549 cells (see e.g. WO 98/39411, U.S. Pat. No. 5,891,690), GH329:HeLa (Gao et al, 2000, Human Gene Therapy 11: 213-219), 293, and the like. In certain embodiments, the producer cells are for instance HEK293 cells, or PER.C6 cells, or 911 cells, or IT293SF cells, and the like.

For non-subgroup C E1-deficient adenoviruses such as HAdV35 (subgroup B) or HAdV26 (subgroup D), it is preferred to exchange the E4-orf6 coding sequence of these non-subgroup C adenoviruses with the E4-orf6 of an adenovirus of subgroup C such as HAdV5. This allows propagation of such adenoviruses in well known complementing cell lines that express the E1 genes of Ad5, such as for example 293 cells or PER.C6 cells (see, e.g. Havenga et al, 2006, J. Gen. Virol. 87: 2135-2143; WO 03/104467, incorporated in its entirety by reference herein). In certain embodiments, the adenovirus in the vaccine composition is a human adenovirus of serotype 35, with a deletion in the E1 region, and with an E4-orf6 region of HAdV5. In certain embodiments, an adenovirus that can be used is a human adenovirus of serotype 26, with a deletion in the E1 region, and with an E4-orf6 region of HAdV5.

In alternative embodiments, there is no need to place a heterologous E4-orf6 region (e.g. of HAdV5) in the adenoviral vector, but instead the E1-deficient non-subgroup C vector is propagated in a cell line that expresses both E1 and a compatible E4-orf6, e.g. the 293-ORF6 cell line that expresses both E1 and E4-orf6 from Ad5 (see e.g. Brough et al, 1996, J Virol 70: 6497-501 describing the generation of the 293-ORF6 cells; Abrahamsen et al, 1997, J Virol 71: 8946-51 and Nan et al, 2003, Gene Therapy 10: 326-36 each describing generation of E1 deleted non-subgroup C adenoviral vectors using such a cell line).

Alternatively, a complementing cell that expresses E1 from the serotype that is to be propagated can be used (see e.g. WO 00/70071, WO 02/40665).

For subgroup B adenoviruses, such as HAdV35, having a deletion in the E1 region, it is preferred to retain the 3' end of the E1B 55K open reading frame in the adenovirus, for instance the 166 bp directly upstream of the pIX open reading frame or a fragment comprising this such as a 243 bp fragment directly upstream of the pIX start codon (marked at the 5' end by a Bsu36I restriction site in the HAdV35 genome), since this increases the stability of the adenovirus because the promoter of the pIX gene is partly residing in this area (see, e.g. Havenga et al, 2006, J. Gen. Virol. 87: 2135-2143; WO 2004/001032, incorporated by reference herein).

In certain embodiments, the recombinant HAdV26 or HAdV35 vectors of the invention comprise as the 5' terminal nucleotides the nucleotide sequence: CTATCTAT. These embodiments are advantageous because such vectors display improved replication in production processes, resulting in batches of adenovirus with improved homogeneity, as compared to vectors having the original 5' terminal sequences (generally CATCATCA) (see also patent application nos. PCT/EP2013/054846 and U.S. Ser. No. 13/794, 318, entitled 'Batches of recombinant adenovirus with altered terminal ends' filed on 12 Mar. 2012 in the name of Crucell Holland B. V.), incorporated in its entirety by reference herein. The invention thus also provides batches of recombinant adenovirus encoding an antigenic fragment of a HPV L2 protein or a part thereof, wherein the adenovirus is a human adenovirus serotype 4, 11, 26, 35, 48, 49, 50 and wherein essentially all (e.g. at least 90%) of the adenoviruses in the batch comprise a genome with terminal nucleotide sequence CTATCTAT.

The term 'about' for numerical values as used in the present disclosure means the value ±10%.

In certain embodiments, the invention provides methods for making a vaccine against HPV comprising providing a recombinant adenoviral vector comprising capsid protein IX fused to an antigen comprising antigenic fragments of a L2 protein of HPV, propagating said recombinant adenovirus in a culture of host cells, isolating and purifying the recombinant adenovirus, and bringing the recombinant adenovirus in a pharmaceutically acceptable composition.

Recombinant adenovirus can be prepared and propagated in host cells, according to well known methods, which entail cell culture of the host cells that are infected with the adenovirus. The cell culture can be any type of cell culture, including adherent cell culture, e.g. cells attached to the surface of a culture vessel or to microcarriers, as well as suspension culture.

Most large-scale suspension cultures are operated as batch or fed-batch processes because they are the most straightforward to operate and scale up. Nowadays, continuous processes based on perfusion principles are becoming more common and are also suitable (see e.g. WO 2010/060719, and WO 2011/098592, both incorporated by reference herein, which describe suitable methods for obtaining and purifying large amounts of recombinant adenoviruses).

Producer cells are cultured to increase cell and virus numbers and/or virus titers. Culturing a cell is done to enable it to metabolize, and/or grow and/or divide and/or produce virus of interest according to the invention. This can be accomplished by methods as such well known to persons skilled in the art, and includes but is not limited to providing nutrients for the cell, for instance in the appropriate culture media. Suitable culture media are well known to the skilled person and can generally be obtained from commercial sources in large quantities, or custom-made according to standard protocols. Culturing can be done for instance in dishes, roller bottles or in bioreactors, using batch, fed-batch, continuous systems and the like. Suitable conditions for culturing cells are known (see e.g. Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9).

Typically, the adenovirus will be exposed to the appropriate producer cell in a culture, permitting uptake of the virus. Usually, the optimal agitation is between about 50 and 300 rpm, typically about 100-200, e.g. about 150, typical DO is 20-60%, e.g. 40%, the optimal pH is between 6.7 and 7.7, the optimal temperature between 30 and 39° C., e.g. 34-37° C., and the optimal MOI between 5 and 1000, e.g. about 50-300. Typically, adenovirus infects producer cells spontaneously, and bringing the producer cells into contact with recombinant adenoviral particles is sufficient for infection of the cells. Generally, an adenovirus seed stock is added to the culture to initiate infection, and subsequently the adenovirus propagates in the producer cells. This is all routine for the person skilled in the art.

After infection with an adenovirus, the virus replicates inside the cell and is thereby amplified, a process referred to herein as propagation of adenovirus. Adenovirus infection results finally in the lysis of the cells being infected. The lytic characteristics of adenovirus therefore permits two different modes of virus production. The first mode is harvesting virus prior to cell lysis, employing external factors to lyse the cells. The second mode is harvesting virus supernatant after (almost) complete cell lysis by the produced virus (see e.g. U.S. Pat. No. 6,485,958, describing the harvesting of adenovirus without lysis of the host cells by an external factor). It is preferred to employ external factors to actively lyse the cells for harvesting the adenovirus.

Methods that can be used for active cell lysis are known to the person skilled in the art, and have for instance been discussed in WO 98/22588, p. 28-35. Useful methods in this respect are for example, freeze-thaw, solid shear, hypertonic and/or hypotonic lysis, liquid shear, sonication, high pressure extrusion, detergent lysis, combinations of the above, and the like. In one embodiment of the invention, the cells are lysed using at least one detergent. Use of a detergent for lysis has the advantage that it is an easy method, and that it is easily scalable.

Detergents that can be used, and the way they are employed, are generally known to the person skilled in the art. Several examples are for instance discussed in WO 98/22588, p. 29-33. Detergents can include anionic, cationic, zwitterionic, and nonionic detergents. The concentration of the detergent may be varied, for instance within the range of about 0.1%-5% (w/w). In one embodiment, the detergent used is Triton X-100.

Nuclease may be employed to remove contaminating, i.e. mostly from the producer cell, nucleic acids. Exemplary nucleases suitable for use in the present invention include Benzonase®, Pulmozyme®, or any other DNase and/or RNase commonly used within the art. In preferred embodiments, the nuclease is Benzonase®, which rapidly hydrolyzes nucleic acids by hydrolyzing internal phosphodiester bonds between specific nucleotides, thereby reducing the viscosity of the cell lysate. Benzonase® can be commercially obtained from Merck KGaA (code W214950). The concentration in which the nuclease is employed is preferably within the range of 1-100 units/ml. Alternatively, or in addition to nuclease treatment, it is also possible to selectively precipitate host cell DNA away from adenovirus preparations during adenovirus purification, using selective precipitating agents such as domiphen bromide (see e.g. U.S. Pat. No. 7,326,555; Goerke et al., 2005, Biotechnology and bioengineering, Vol. 91: 12-21; WO 2011/045378; WO 2011/045381).

Methods for harvesting adenovirus from cultures of producer cells have been extensively described in WO 2005/080556.

In certain embodiments, the harvested adenovirus is further purified. Purification of the adenovirus can be performed in several steps comprising clarification, ultrafiltration, diafiltration or separation with chromatography as described in for instance WO 05/080556, incorporated by reference herein. Clarification may be done by a filtration step, removing cell debris and other impurities from the cell lysate. Ultrafiltration is used to concentrate the virus solution. Diafiltration, or buffer exchange, using ultrafilters is a way for removal and exchange of salts, sugars and the like. The person skilled in the art knows how to define the optimal conditions for each purification step. Also WO 98/22588, incorporated in its entirety by reference herein, describes methods for the production and purification of adenoviral vectors. The methods comprise growing host cells, infecting the host cells with adenovirus, harvesting and lysing the host cells, concentrating the crude lysate, exchanging the buffer of the crude lysate, treating the lysate with nuclease, and further purifying the virus using chromatography.

Preferably, purification employs at least one chromatography step, as for instance discussed in WO 98/22588, p. 61-70. Many processes have been described for the further purification of adenoviruses, wherein chromatography steps are included in the process. The person skilled in the art will be aware of these processes, and can vary the exact way of employing chromatographic steps to optimize the process. It is for instance possible to purify adenoviruses by anion exchange chromatography steps, see for instance WO 2005/080556 and Konz et al, 2005, Hum Gene Ther 16: 1346-1353. Many other adenovirus purification methods have been described and are within the reach of the skilled person. Further methods for producing and purifying adenoviruses are disclosed in for example (WO 00/32754; WO 04/020971; U.S. Pat. Nos. 5,837,520; 6,261,823; WO 2006/108707; Konz et al, 2008, Methods Mol Biol 434: 13-23; Altaras et al, 2005, Adv Biochem Eng Biotechnol 99: 193-260), all incorporated by reference herein.

Another aspect of the present invention relates to a vaccine comprising a recombinant adenoviral vector or a composition according to the present invention, further comprising a pharmaceutically acceptable excipient.

The term "vaccine" refers to an agent or composition containing an active component effective to induce a therapeutic degree of immunity in a subject against a certain pathogen or disease. In the present invention, the vaccine comprises an effective amount of a recombinant adenovirus that comprises a capsid protein IX fused to an antigen that comprises antigenic fragments of a Human Papillomavirus (HPV) L2 protein, which results in an immune response against the HPV L2 protein. The term "vaccine" according to the invention implies that it is a pharmaceutical composition, and thus typically includes a pharmaceutically acceptable diluent, carrier or excipient. It may or may not comprise further active ingredients. In certain embodiments it may be a combination vaccine that further comprises other components that induce an immune response, e.g. against other proteins and/or against other infectious agents.

For administering to humans, the invention may employ pharmaceutical compositions comprising the adenovirus and a pharmaceutically acceptable carrier or excipient. In the present context, the term "Pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The purified Ad preferably is formulated and administered as a sterile solution although it is also possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g pH 5.0 to 7.5. The Ad typically is in a solution having a suitable pharmaceutically acceptable buffer, and the solution of Ad may also contain a salt. Optionally stabilizing agent may be present, such as albumin. In certain embodiments, detergent is added. In certain embodiments, Ad may be formulated into an injectable preparation. These formulations contain effective amounts of Ad, are either sterile liquid solutions, liquid suspensions or lyophilized versions and optionally contain stabilizers or excipients. An adenovirus vaccine can also be aerosolized for intranasal administration (see e.g. WO 2009/117134).

For instance, adenovirus may be stored in the buffer that is also used for the Adenovirus World Standard (Hoganson et al, Development of a stable adenoviral vector formulation, Bioprocessing March 2002, p. 43-48): 20 mM Tris pH 8, 25 mM NaCl, 2.5% glycerol. Another useful formulation buffer suitable for administration to humans is 20 mM Tris, 2 mM MgCl2, 25 mM NaCl, sucrose 10% w/v, polysorbate-80 0.02% w/v. Obviously, many other buffers can be used, and several examples of suitable formulations for the storage and for pharmaceutical administration of purified (adeno)virus preparations can for instance be found in European patent no. 0853660, U.S. Pat. No. 6,225,289 and in international patent applications WO 99/41416, WO 99/12568, WO 00/29024, WO 01/66137, WO 03/049763, WO 03/078592, WO 03/061708.

In certain embodiments a composition comprising the adenovirus further comprises one or more adjuvants. Adjuvants are known in the art to further increase the immune response to an applied antigenic determinant, and pharmaceutical compositions comprising adenovirus and suitable adjuvants are for instance disclosed in WO 2007/110409, incorporated by reference herein. The terms "adjuvant" and "immune stimulant" are used interchangeably herein, and are defined as one or more substances that cause stimulation of the immune system. In this context, an adjuvant is used to enhance an immune response to the adenovirus vectors of the invention. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as E. coli heat labile enterotoxin LT, cholera toxin CT, and the like. It is also possible to use vector-encoded adjuvant, e.g. by using heterologous nucleic acid that encodes a fusion of the oligomerization domain of C4-binding protein (C4bp) to the antigen of interest (e.g. Solabomi et al, 2008, Infect Immun 76: 3817-23). In certain embodiments the compositions of the invention comprise aluminium as an adjuvant, e.g. in the form of aluminium hydroxide, aluminium phosphate, aluminium potassium phosphate, or combinations thereof, in concentrations of 0.05-5 mg, e.g. from 0.075-1.0 mg, of aluminium content per dose.

In other embodiments, the compositions do not comprise adjuvants. It is also possible according to the invention to administer further active components, in combination with the vaccines according to the invention. Such further active components may comprise e.g. other HPV antigens or vectors comprising nucleic acid encoding these. Such vectors may be non-adenoviral or adenoviral, of which the latter can be of any serotype. An example of other HPV antigens includes HPV proteins or immunologically active parts thereof. Further active components may also comprise non-HPV antigens, e.g. from other pathogens such as viruses, bacteria, parasites, and the like. The administration of further active components may for instance be done by separate administration or by administering combination products of the vaccines of the invention and the further active components. In certain embodiments, further non-adenoviral antigens, may be encoded in the vectors of the invention. In certain embodiments, it may thus be desired to express more than one protein from a single adenovirus, and in such cases more coding sequences for instance may be linked to form a single transcript from a single expression cassette or may be present in two separate expression cassettes cloned in different parts of the adenoviral genome.

A further aspect of the invention relates to the use of a vaccine according to the invention in the therapeutic, prophylactic or diagnostic treatment of HPV. The invention also relates to a method of inducing an immune response in a subject, comprising administering an adenoviral vector or vaccine as described herein. Adenovirus compositions may be administered to a subject, e.g. a human subject. The total dose of the adenovirus provided to a subject during one administration can be varied as is known to the skilled practitioner, and is generally between $1\times10^7$ viral particles (VP) and $1\times10^{12}$ VP, preferably between $1\times10^8$ VP and $1\times10^{11}$ VP, for instance between $3\times10^8$ and $5\times10^{10}$ VP, for instance between $10^9$ and $3\times10^{10}$ VP.

Administration of adenovirus compositions can be performed using standard routes of administration. Non-limiting embodiments include parenteral administration, such as by injection e.g. intradermal, intramuscular, etc, or subcutaneous, transcutaneous, or mucosal administration, e.g. intranasal, oral, and the like. It is preferred according to the present invention to administer the vaccine intramuscularly. The advantage of intramuscular administration is that it is simple and well-established, and does not carry the safety concerns for intranasal application in infants younger than 6 months. In one embodiment a composition is administered by intramuscular injection, e.g. into the deltoid muscle of the arm, or vastus lateralis muscle of the thigh. The skilled person knows the various possibilities to administer a composition, e.g. a vaccine in order to induce an immune response to the antigen(s) in the vaccine.

A subject as used herein preferably is a mammal, for instance a rodent, e.g. a mouse, a cotton rat, or a non-human-primate, or a human. Preferably, the subject is a human subject. The subject can be of any age, e.g. from about 1 month to 100 years old, e.g. from about 2 months to about 80 years old, e.g. from about 1 month to about 3 years old, from about 3 years to about 50 years old, from about 50 years to about 75 years old, etc.

It is also possible to provide one or more booster administrations of one or more adenovirus vaccines of the invention. If a boosting vaccination is performed, typically, such a boosting vaccination will be administered to the same subject at a moment between one week and one year, preferably between two weeks and four months, after administering the composition to the subject for the first time (which is in such cases referred to as 'priming vaccination'). In alternative boosting regimens, it is also possible to administer different vectors, e.g. one or more adenoviruses of different serotype, or other vectors such as MVA, or DNA, or protein, to the subject after the priming vaccination. It is for instance possible to administer to the subject a recombinant adenoviral vector according to the invention as a prime, and boosting with a composition comprising a HPV protein.

In certain embodiments, the administration comprises a priming and at least one booster administration. In certain embodiments thereof, the priming administration is with a HAdV35 comprising nucleic acid encoding a HPV protein according to the invention and the booster administration is with a HAdV26 comprising nucleic acid encoding said HPV protein. In other embodiments thereof, the priming administration is with HAdV26 and the booster administration is with HAdV35. In other embodiments, both the priming and booster administration are with HAdV35. In certain embodiments, the priming administration is with HAdV35 and the booster administration is with a HPV protein. In all these embodiments, it is possible to provide further booster administrations with the same or other vectors or protein.

In certain embodiments, the administration comprises a single administration of a recombinant adenovirus according to the invention, without further (booster) administrations. Such embodiments are advantageous in view of the reduced complexity and costs of a single administration regimen as compared to a prime-boost regimen. Complete protection is already observed after single administration of the recombinant adenoviral vectors of the invention without booster administrations in the cotton rat model in the examples herein.

The invention is further explained in the following examples. The examples do not limit the invention in any way. They merely serve to clarify the invention.

EXAMPLES

Example 1: HPV L2 Antigen Concatemer Fused to pIX by Capsid Incorporation

Efficient Capsid Incorporation of the pIX-Sx3 and pIX-Sx4 HPV L2 Concatemers

In order to assess whether different HPV L2 concatemers can be fused to pIX and efficiently incorporated into the capsid, a number of different pIX modified HPV L2 display vectors were designed, generated and assessed for capsid incorporation (FIG. 1).

Antigen Design

The Human Papillomavirus L2 protein concatemers (i.e. motifs) are encoded in the genome and displayed via the protein IX (pIX) on the Adenoviral capsid. L2 protein fragments of the different HPV types, either the (S) 10-40 amino acids motif (or 60-90/100-130 a.a.), the (L) 10-89 amino acids motif or a combination thereof (SSL) are used to generate the L2 concatemers. These concatemers are then fused to pIX via a small hinge linker consisting of three consecutive glycine amino acids (3-Gly). The selected regions from the L2 protein contain either one or two conserved linear neutralizing antibody epitopes (or antigenic fragment), namely the amino acid residues 17-36 (S and L design) or the amino acid residues 69-81 (L design)(FIG. 1A), previously shown to be necessary for generation of L2 based protection against HPV infection (review: Karanam et al. Imm. Cell Bio. 2009).

Recombinant Human Adenovirus Vector (HAdV) Generation

The replication deficient recombinant human Adenovirus 35 (HAdV-35) and Human Adenovirus 26 (HAdV-26) vectors encoding and displaying the pIX-L2 concatemers are generated as previously described by Havenga et al. 2006. The pIX-L2 modifications are genetically inserted into the left part of the HAdV-genome (pAdapt35.Bsu/pShuttle26 plasmids). The rescue of the vectors was subsequently performed in the E1-complementing PER.C6® cell line by transfecting linearized pAdapt or pShuttle and the cosmids (the rigt part of the genome) with Lipofectamine (Invitrogen). The vectors were subsequently plaque purified and propagated on PER.C6® cells supplemented with 10% of fetal bovine serum (Life Technologies Inc.) and 10 mM MgCl$_2$. A large panel of either HAdV-35 or HAdV-26 vectors encoding and displaying the different HPV L2 concatemers was generated, cesium purified and characterized. The viral titers, viral particles (VP)/ml, infectious unit (IU)/ml, and the corresponding VP/IU ratio and VP/cm$^2$ were determined for each purified batch. These characteristics were comparable to the respective control vector (i.e. non-modified pIX) and thus show that the producibility of the pIX-modified vectors remains unaffected by the addition of the L2 concatemer (data not shown).

pIX-L2 Capsid Incorporation Efficiency pIX-L2 HPV capsid incorporation efficiency was evaluated in order to determine which of the pIX-fusion proteins designs are the most optimal, in terms of generating vectors with incorporation efficiency comparable to the non-modified pIX vector. For that reason the pIX-L2 vectors were compared to non-modified-pIX control vectors (HAdV.empty). To determine the pIX-L2 content in the viral capsid and the efficiency of the capsid incorporation, a number of analyses were performed on purified viral batches including Western Blot, ELISA and UPLC/MS analysis.

Initially, the optimal HPV L2 concatemer design was determined. For this purpose HAdV-35 vectors encoding the pIX-Gly-L2(Sx3)45.18.16 (93 amino acids), pIX-Gly-L2 (Sx3)x3)45.18.16 (273 amino acids) pIX-Gly-L2(Lx3) 45.18.16 (238 amino acids) and pIX-Gly-L2(Sx2+L) 45.18.16 (418 amino acids) were generated (FIG. 1B) and purified. The purified viral particles were subsequently analyzed by Western blot and confirmed by Ultra Performance Liquid Chromatography/Mass spectrometry UPLC/MS to determine the exact content of pIX-L2 protein in the capsid.

Western Blot Analysis of the Capsid Incorporated pIX-L2 Fusion Proteins

Western blot (WB) analysis of the capsid incorporated pIX-L2 variants was performed by reducing and denaturing purified viral particles and loading them on gel at $1.5 \times 10^{10}$, $0.5 \times 10^{10}$ and $0.17 \times 10^{10}$ viral particles per well (VP/well) concentration. The viral particles were then separated on pre-cast 12% Bis/Tris Nu-PAGE gel (Invitrogen) in MOPS buffer (Invitrogen) at 175 V, 500 mA. Size separated proteins were subsequently transferred to a nitrocellulose membrane according to manufacturer's recommendations using iBlot® Transfer stacks (iBlot system; Invitrogen). The pIX-L2 protein content was determined by staining the membranes for 1 hour with anti-L2 specific serum (HPV 16 mouse serum) or anti-pIX monoclonal antibody (6740) and anti-fiber monoclonal antibody (Ad5 4D2, Abcam) as a loading control in 5% non-fat dry milk (BioRad)/Tris buffered Saline Tween 20 (Invitrogen). Visualization of the protein of interest was achieved by staining with the fluorescently labeled secondary antibody IRDye800CW® 1:10 000 goat anti-mouse and recorded on the Odyssey® (Li-Cor).

Major differences in capsid incorporation were observed on the Western Blot (Table 1) between the HPV L2 45.18.16 concatemers Sx3, (Sx3)x3, Lx3, (Sx2)+L fused to the pIX via a Gly linker. The direct comparison between the vectors shows good capsid incorporation of the Sx3 variant. (Sx3)x3 and Lx3 variants were detected in the purified batches, however to a much lesser extent. In contrast, the (Sx2)+L was not detected at all in the Western Blot analysis using the L2-specific mouse serum (Table 1). These observations indicate that the type of HPV L2 concatemer fused to pIX can influence the capsid incorporation efficiency. The size and possibly the charge seemed to play an important role in the capsid incorporation efficiency. The (Sx3) 93 amino acids configuration was most efficiently incorporated, whereas the (Sx2)+L 418 amino acids configuration was not incorporated at all. Based on the efficient capsid incorporation, the L2 concatemer (Sx3) containing the 10-40 amino acids of the HPV 45, 18 and 16 L2 protein fused to pIX via a Gly-linker was selected as most optimal (SEQ ID NO 1).

TABLE 1

Capsid incorporation pIX-modifications.

| | Modification | | pIX fusion | Capsid incorporation (n) | |
|---|---|---|---|---|---|
| | E1-region | pIX | a.a. | WB | ELISA |
| HAdV26 | | | | | |
| Advac © | Empty | 52.33.31.45.18.16 (S × 6) | 183 | ++ (3) | ND |
| | Empty | 33.31.45.18.16 (S × 5) | 153 | +++ (3) | ND |
| | Empty | 52.31.45.18.16 (S × 5) | 153 | +++ (3) | ND |
| | Empty | 33.45.18.16 (S × 4) | 123 | ++++ (3) | ND |
| | Empty | 31.45.18.16 (S × 4) | 123 | ++++ (3) | ND |
| | Empty | 45.18.16 (S × 3) | 93 | ++++ (1) | ND |
| | Empty | SP1-45.18.16 (L × 3) | 302 | Not detected | ND |
| HAdV35 | | | | | |
| Advac © | Empty | 45.18.16 (S × 3) | 93 | ++++ (4) | ++++ (2) |
| | Empty | 6.31.33.16 (S × 4) | 123 | ++++ (2) | ++++ (2) |
| | Empty | 11.52/58.45.18 (S × 4) | 123 | ++++ (2) | ++++ (2) |
| Batch 2 | Empty | 6.31.33.16 (S × 4) | 123 | ++++ (1) | ND |
| Batch 2 | Empty | 11.52/58.45.18 (S × 4) | 123 | ++++ (1) | ND |
| | Empty | (NR) 6.31.33.16 (S × 4) | 123 | ND | ND |
| | Empty | (NR) 11.52/58.45.18 (S × 4) | 123 | ND | ND |
| | ΔCMV.pA | 6.31.33.16 (S × 4) | 123 | ++++ (1) | ++++ (2) |
| | ΔCMV.pA | 11.52/58.45.18 (S × 4) | 123 | ++++ (1) | ++++ (2) |
| | Empty | 45.18.16 ((S × 3) × 3) | 273 | +/− (2) | ND |
| | Empty | 45.18.16 (L × 3) | 238 | +/− (2) | ND |
| | Empty | 45.18.16 ((S × 2) + L) | 418 | Not detected | ND |

Figure 2A:
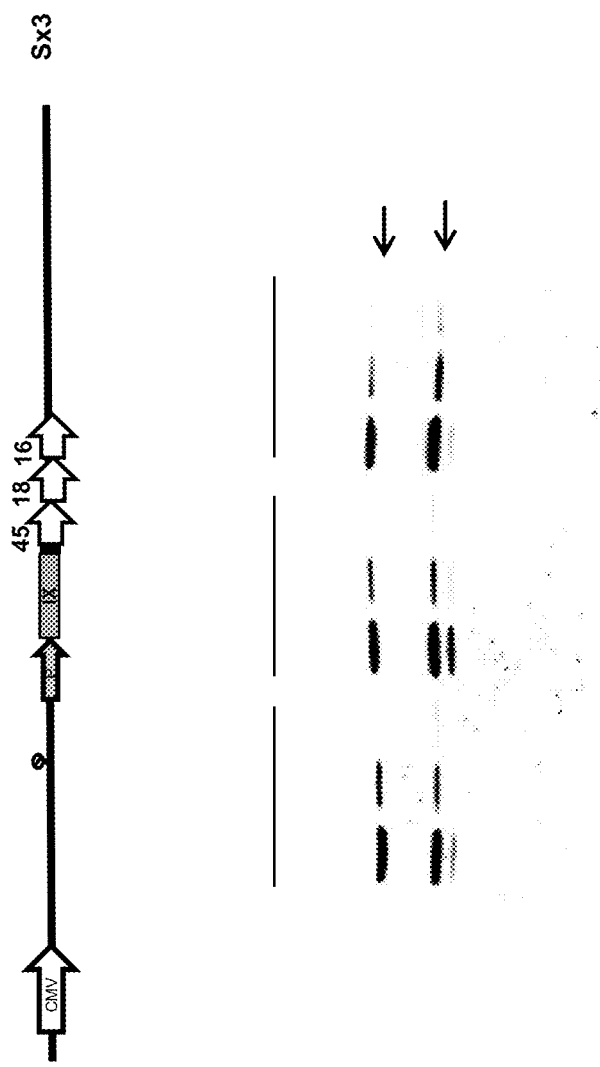
FIG. 2: Capsid incorporation of the HPV L2 (Sx3) design. (A) pIX-Sx3 capsid incorporation was determined by Western blot. Three different batches of HAdV35.Empty.pIX-L2 (Sx3) purified vector preparations (at three different concentrations: $1.5 \times 10^{10}$, $1 \times 10^{10}$ and $0.17 \times 10^{10}$ VP/well) were separated on gel, blotted and stained with an anti-pIX (6740) monoclonal antibody (pIX-Sx3, 25 kDa) and an anti-fiber antibody (HAdV fiber knob, 4D2) as a loading control (35 kDa). (B) pIX-Sx3 capsid incorporation determined by RP-UPLC analysis. Purified HAdV35.Empty (non-modified protein IX) and HAdV35.Empty.pIX-Sx3 ($2.5 \times 10^{11}$ VP) were loaded onto a C4 column (ACN+0.17% TFA gradient) and measured at $OD_{280}$ absorption units (AU). The RP-UPLC proteome analysis of purified HAdV35.Empty non-modified pIX control (top panel) vector and the HAdV35 Sx3 pIX-L2 45.18.16 (lower panel). The detected viral proteins are indicated by the Roman numbers (II-X) according to their elution time (x-axis) in minutes and $OD_{280}$ absorption units (AU) (y-axis). The two arrows (number 1 and 2) indicate the peaks that were not detected for the control HAdV35.Empty vector.

++++: very good,
+++: good,
++: poor,
+: barely detected and
−: not detected
(n) = number of experiments,
a.a.: amino acids,
NR: non-reduced inter-epitope homology,
ND: not determined The selected pIX-L2(S)45.18.16 HAdV-35 vector was further analyzed by Western Blot to determine the batch to batch variation in terms of capsid incorporation efficiency. For this purpose two additional batches were generated, purified, and compared individually to the HAdV35.Empty vector (data not shown) and to each other. After staining with the anti-pIX monoclonal antibody (6740) and the anti-fiber monoclonal antibody (4D2) (~35 kDa), comparable band intensities of the pIX-L2(Sx3)45.18.16 (~25 kDa) were observed amongst all three batches (FIG. 2A). Thus, no apparent batch to batch variation was observed between three batches of HAdV35.Empty.pIX-L2(Sx3) 45.18.16 in terms of pIX-L2(Sx3) capsid incorporation efficiency.

Figure 2B:
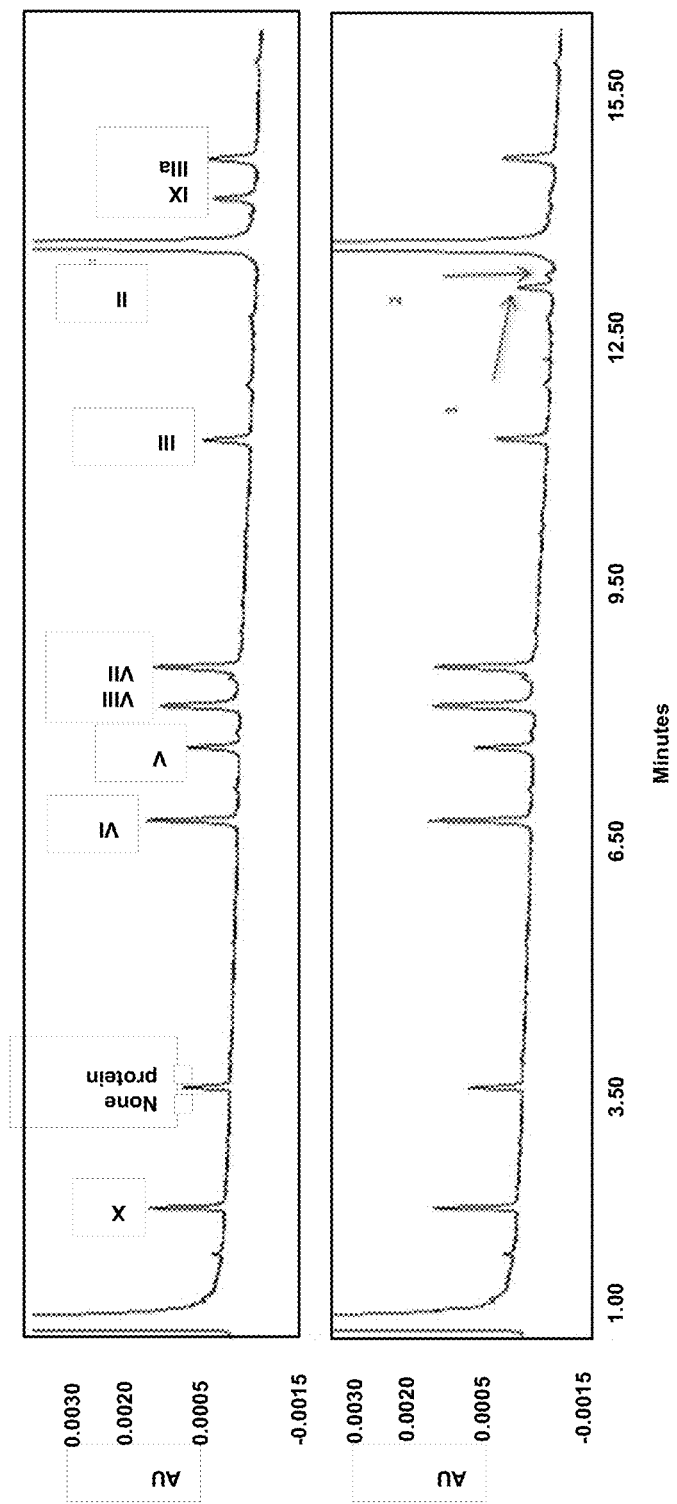

Reversed Phase-UPLC Analysis of HAdV-35.Empty.pIX-L2(Sx3)45.18.16 to Confirm the Capsid Incorporation Efficiency In order to confirm the comparable levels of native pIX in HAdV35.Empty (non-modified pIX) and HAdV35.Emtpy.pIX-L2(Sx3)45.18.16 observed in Western Blot analysis, the vectors were tested in parallel by Reversed Phase Ultra Performance Liquid Chromatography (RP-UPLC). Here a total of 2.5×10¹¹ VP/ml purified batches were loaded on a RP-UPLC C4 column with the acetonitrile (ACN)+0.17% and trifluoroacetic acid (TFA) gradient. The absorption was measured at 280 nm. The obtained HAdV35 proteome, where each peak corresponds to a viral protein and its corresponding elution time is shown in FIG. 2B. The analysis of the non-modified pIX HAdV35.Empty control (top panel) clearly shows a pIX peak at ~14 min elution time. As expected, this pIX peak is not detected in the HAdV35.Empty.pIX-L2(Sx3)45.18.16 analysis (lower panel). Instead, two additional peaks eluting at ~13 min were observed (see arrows on lower graph). These are expected to represent the pIX-L2(Sx3)45.18.16 protein (FIG. 2B). The relative amount (in percentage) of pIX and pIX-L2 (peak area) was calculated by determining the total amount of all viral proteins (sum of peak area) and calculating the percentage of the pIX quantity (peak area). The loading was controlled by correction with the penton base (protein III) peak area (eluting at ~12 minutes). In HAdV35.empty, pIX constituted 2.7% of the total viral protein. In HAdV35.Empty.pIX-L2(Sx3)45.18.16, the pIX-L2(Sx3) major peak accounted for 2.1% and the minor peak 0.4% of the total viral protein (total of 2.5%). In short, this analysis confirms the presence of a comparable level of pIX (2.7 vs. 2.5%) in both the HAdV35.Empty and HAdV35.Empty.pIX-L2(Sx3)45.18.16. Thus, the addition of the L2(S)45.18.16 HPV concatemer allows for an efficient pIX-L2 capsid incorporation.

HAdV-35.Empty~pIX-L2(Sx3)45.18.16 Minor Band Confirmation by LC-MS Analysis

Since both the Western Blot and RP-UPLC analyses of pIX-L2(S)45.18.16 showed a second minor band/peak, the exact sequence of this band was determined by Liquid Chromatography Mass Spec (LC-MS) analysis. Purified HAdV35.Empty and HAdV35.Empty.pIX-L2(Sx3)45.18.16 were loaded on a SDS-PAGE gel under reducing conditions followed by a MS compatible SilverQuest™ staining (Thermo Fisher Scientific) according to manufacturer's recommendations. The in-gel digestion by Trypsin of the pooled pIX bands was performed as recommended by the manufacturer (Thermo Fisher Scientific). The digested bands were then separated on a reversed phase C18 BEH300 column with 2-50% ACN+0.1% FA gradient and the MSE analysis was performed on a Synapt G2 ESI-Q-TOF mass spectrometer. The results show, that the major band/peak (25 kDa in Western Blot and ~13 min elution time in RP-UPLC), is indeed the full pIX-L2(Sx3)45.18.16. The minor band/peak (~24 kDa in Western Blot and ~13.5 min elution time in RP-UPLC), was determined to be pIX-L2(Sx3)45.18. These results indicate that in a small fraction of the capsid incorporated pIX-L2(Sx3), the distally oriented HPV 16 10-40 amino acid sequence is missing or possibly is cleaved off.

In addition to the strong linear 17-36 amino acids B-cell epitope, the 10-40 amino acid of the HPV 16 L2 protein, also contains the '.TKR/ASA' sequence, which is one Arginine (R) at P4 short of the full furin recognition site RTKR/ASA (Richards et al. 2006). Most presumably, the presence of this partial furin recognition site (i.e. .TKR/ASA) contributes to the incomplete digestion of the pIX-L2(S)45.18.16 concatemer into pIX-L2(S)45.18 and HPV 16 10-40 amino acids (distal HPV 16 fragment more accessible to furin), and to a lesser extent cleavage of HPV 18 and 45 10-40 amino acids by furin (due to the proximity to the capsid less accessible for furin cleavage).

Figure 1C:
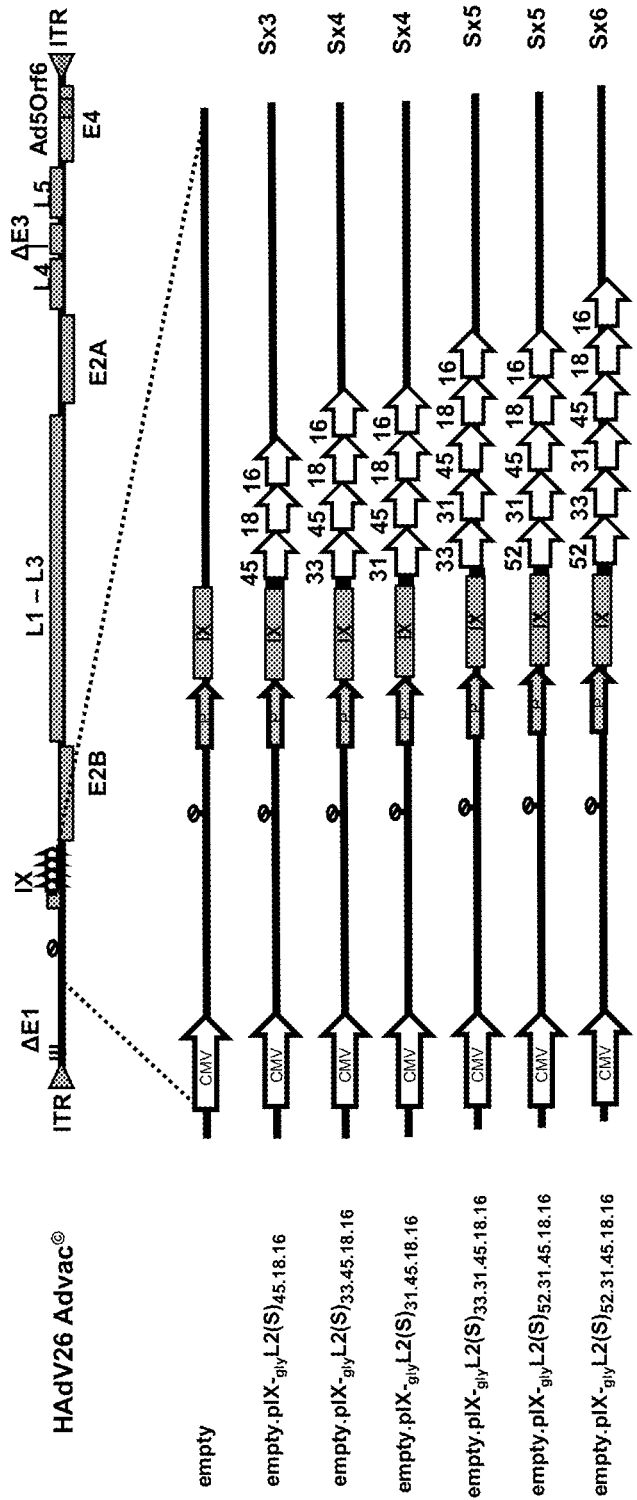
Figure 1D:
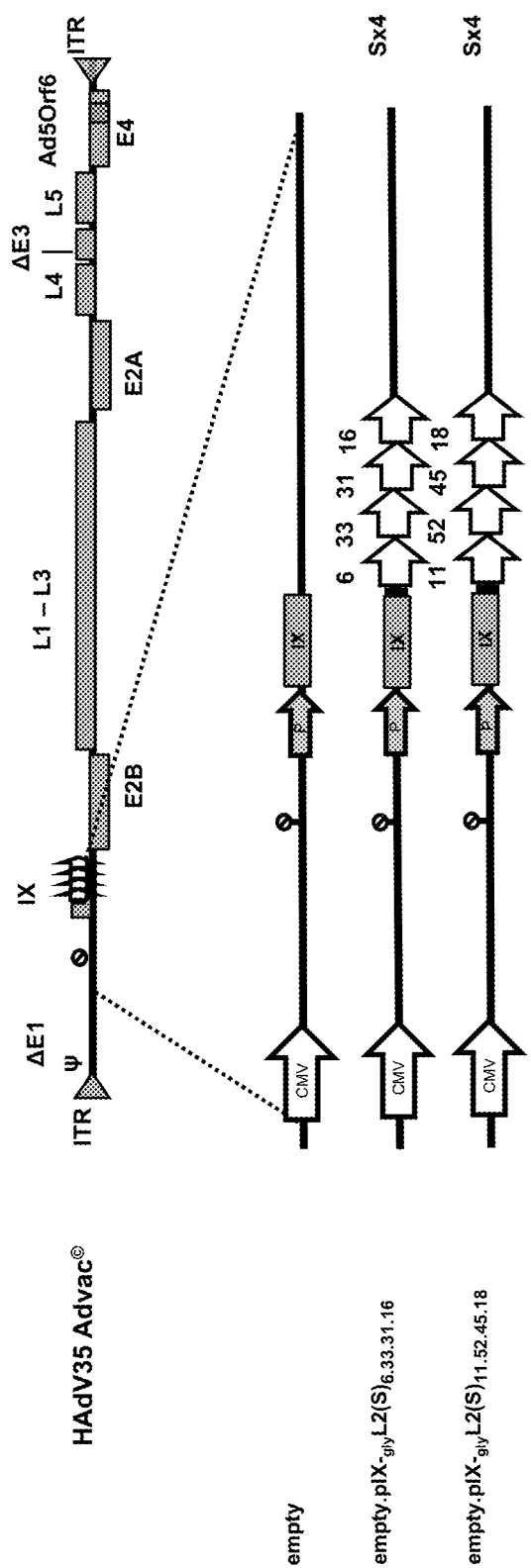

Extending the pIX-L2(S) Design in HAdV26 Vectors by Adding Additional HPV Types to the L2(S)45.18.16 Concatemer Having determined that the L2 protein 10-40 amino acids (Sx3) concatemer design, containing the HPV 45, 18 and 16 fused to pIX via Gly linker, ensures optimal and native pIX capsid loading, we aimed at: (1) assessing how many additional L2 10-40 amino acid sequences from different HPV types could be fused to pIX and still ensure efficient capsid loading; and (2) assessing whether the same modifications can be successfully introduced in other adenoviral types (e.g. HAdV-26). For this purpose, HAdV-26 vectors were generated as indicated above and assessed for capsid incorporation efficiency by Western Blot. Since it was observed in HAdV35 that the pIX-L2((Sx3)x3)45.18.16 showed decreased capsid incorporation (Table 1), the largest (S)-variant tested in HAdV26 was reduced to Sx6. HAdV26 vectors that contain: pIX-L2(Sx3)45.18.16, pIX-L2(Sx4) 31.45.18.16, pIX-L2(Sx4)33.45.18.16, pIX-L2(Sx5) 33.31.45.18.16, pIX-L2(Sx5)52*.31.45.18.16 (*HPV type 52 and 58 are identical in the L2 protein 10-40 amino acids region), and pIX-L2(Sx5)52*.33.31.45.18.16 have been generated (FIG. 1C). Only the clinically relevant cancer causing HPV types were used to generate the pIX-L2 vectors. The capsid incorporation assessment, which used anti-L2 HPV 16 mouse serum and anti-fiber monoclonal antibody (4D2) as loading control, showed some differences between the vectors in incorporation efficiency (Table 1). The vectors were compared to the HAdV35.Empty.pIX-L2 (Sx3)45.18.16 vector and amongst each other to determine the levels of pIX-L2 content. In terms of the pIX-L2 content, both HAdV26.Empty.pIX-L2(Sx3)45.18.16 and HAdV35.Empty.pIX-L2(Sx3)45.18.16 are comparable in Western Blot (Table 1). This observation leads to conclude that regardless of the adenoviral type, the pIX-L2(Sx3) 45.18.16 is efficiently incorporated into the adenoviral vector.

Additionally, the Western Blot analysis shows that the two Sx4 vectors (HAdV-26.Empty.pIX-L2(Sx4)31.45.18.16 (SEQ ID NO: 2) and HAdV-26.Empty.pIX-L2(Sx4) 33.45.18.16 (SEQ ID NO: 3) have comparable pIX content to each other and most importantly to the Sx3 variant (Table 1). The Sx5 variants (HAdV-26.Empty. pIX-L2(Sx5) 33.31.45.18.16 (SEQ ID NO: 4) and HAdV26.Empty.pIX-L2(Sx5)52*.31.45.18.16) (SEQ ID NO: 5) show a slightly decreased capsid incorporation compared to the Sx4 and Sx3 vectors, however they are still efficiently incorporated. The least pIX-L2 content was observed for the Sx6 vector in the HAdV26.Empty.pIX-L2(Sx6)52.33.31.45.18.16 vector. The Sx6 vectors together with the ((Sx3)x3), the Lx3 or the ((Sx2)+L)) vectors showed poor incorporation (table 1). The capsid incorporation of the different (S)-variant vectors shows that in terms of pIX-L2 content the Sx4 variant, closely followed by the Sx5 variant, is the most comparable to the Sx3 modified vector. This observation suggests that much like the Sx3 design, Sx4 as well as the Sx5 variants incorporate efficiently into the adenoviral capsid.

Capsid Incorporation of the Prophylactic HPV HAdV-35 pIX-L2(Sx4) Based Vaccine

Having confirmed that the concatemer which contains four different 10-40 amino acids HPV L2 fragments fused to pIX are efficiently incorporated in the HAdV capsid, two HAdV35 vectors encoding and displaying pIX-L2(S) 6.31.33.16 and pIX-L2(Sx4)11.52/58.45.18 were generated to ensure protection against nine clinically relevant HPV types 6, 11, 16, 18, 31, 33, 45 and 52/58, with the aim to mix in one final vaccine formulation both vectors for a pan-HPV L2 based prophylactic vaccine.

Figure 3A:
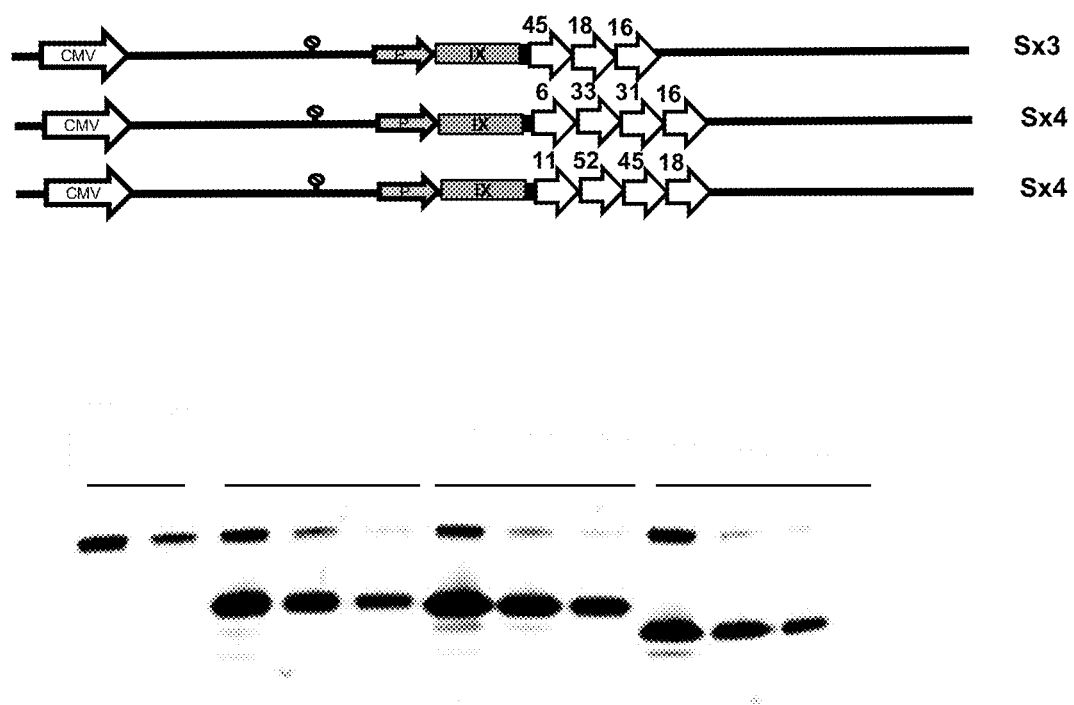

These vectors were produced, as indicated above, in the E1-complementing PER.C6® cells and contain in addition to the encoded pIX-L2(Sx4) modification also an 'Empty' E1-cassette (CMV promoter and SV40 poly A signal), the same as all the previously discussed pIX-mod vectors. The purified HAdV35.Empty.pIX-L2(S)6.31.33.16 and HAdV35.Empty.pIX-L2(S)11.52/58.45.18 vectors were characterized and found to be comparable to non-modified control vectors in terms of viral titers (VP and IU/ml), VP/IU and VP/cm$^2$ (data not shown). The assessment of capsid incorporation by Western blot and staining with the anti-L2 mouse serum (HPV 16 specific) shows that the pIX-L2(S) 6.31.33.16 & pIX-L2(S)11.52/58.45.18 were as efficiently incorporated as the pIX-L2(Sx3)45.18.16 control vector. Additionally, the Western Blot analysis shows comparable capsid incorporation between the pIX-L2(S)6.31.33.16 and pIX-L2(S)11.52/58.45.18 (FIG. 3A). Additional batches of each HAdV35 pIX-L2(Sx4) variant were produced and shown to be comparable for all the characteristics including the capsid incorporation (data not shown). Together, this data indicates that the pIX-L2(S)6.31.33.16 (SEQ ID NO 6) and pIX-L2(S)11.52/58.45.18 (SEQ ID NO: 7) are efficiently incorporated in the HAdV35 capsid without any apparent evident batch to batch variation.

Figure 3B:
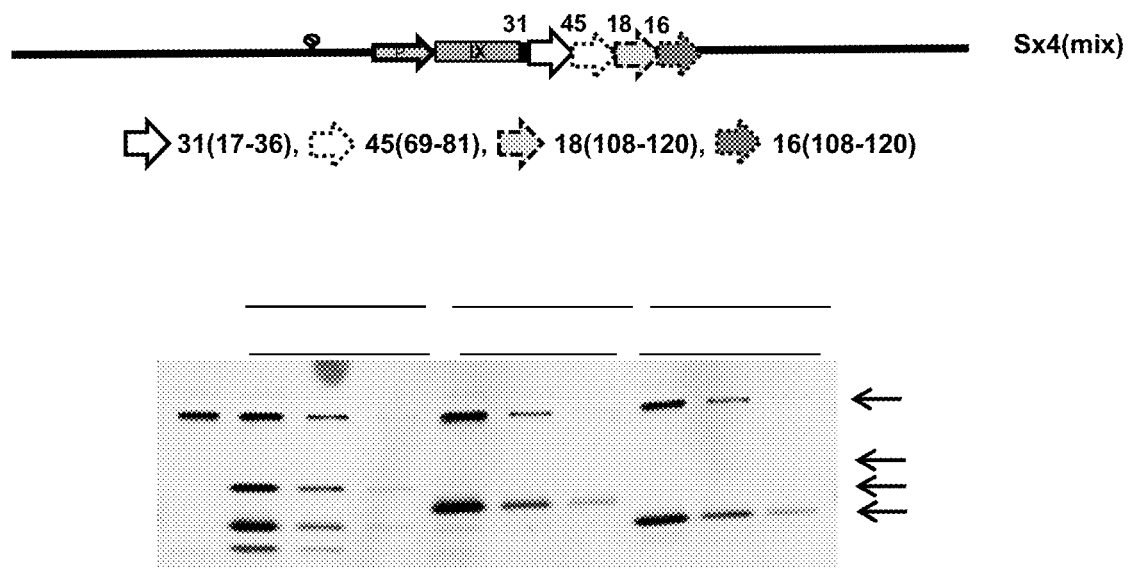

Capsid Incorporation of the pIX-L2(Sx4)mix Containing different L2 Epitope Fragments Since efficient capsid incorporation was confirmed with concatemers containing the HPV L2 10-40 amino acids fragments fused to pIX the design was extended to HAdV26 vectors displaying different L2 epitope fragments within one concatemer, HPV31 (17-36 amino acids), HPV45 (69-81 amino acids), HPV18(108-120 amino acids), and HPV16 (108-120 amino acids) (SEQ ID NO: 8). For this purpose HAdV26.Empty.pIX-L2(Sx4)mix.31.45.18.16 vector was produced, as indicated above, in the E1-complementing PER.C6® cells. The assessment of capsid incorporation by Western blot and staining with the anti-L2 mouse serum (HPV16 specific) and anti-pIX monoclonal shows that the pIX-L2(Sx4)mix.31.45.18.16 was incorporated in the capsid (FIG. 3B). In the Western Blot analysis multiple bands were detected in addition to the 28 kDa pIX-L2(Sx4)

mix.31.45.18.16 protein, suggesting protein cleavage of the L2-concatemer as previously observed.

Nonetheless, this data indicates that the pIX-L2(Sx4) mix.31.45.18.16 (SEQ ID NO: 8) can be incorporated in the HAdV26 capsid.

Example 2: Immunogenicity pIX-L2 Modified Vectors

Figure 4A:
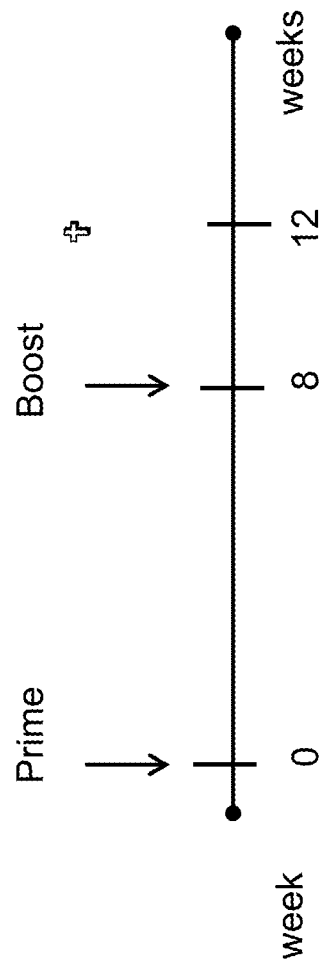
Figure 4B:
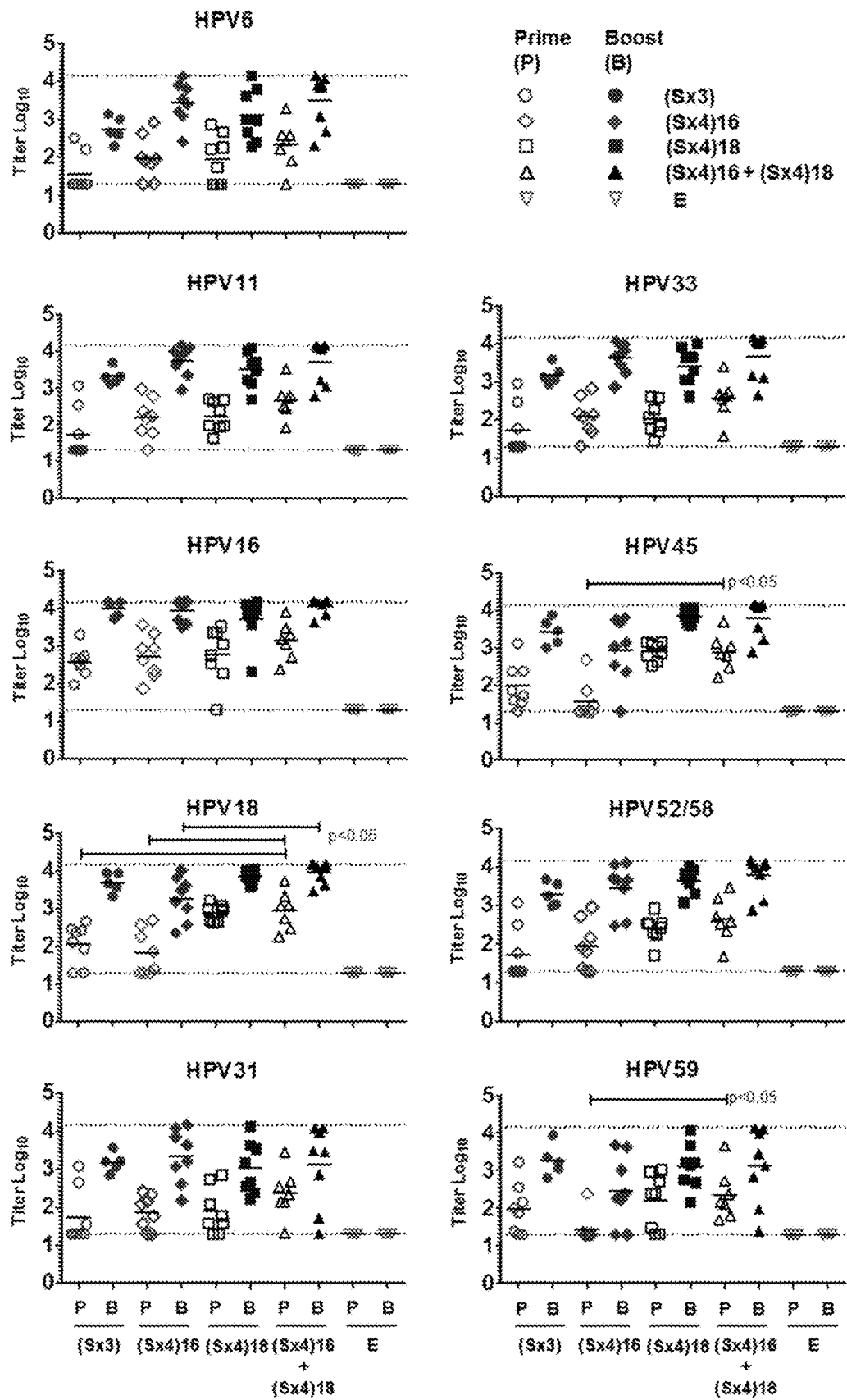

The 9-valent L2 based prophylactic HPV vaccine comprising a mix of two pIX-L2(Sx4) display vectors was evaluated for the induction of HPV type specific antibodies (against antigens included in the vaccine) and cross-reactive antibodies (against antigens not included in the vaccine) in the same experiment as the single HAdV35.Empty.pIX-L2 (Sx4)11.52/58.45.18, HAdV35.Empty.pIX-L2(Sx4) 6.31.33.16 and HAdV35.Empty.pIX-L2(Sx3) vectors. Mice (CB6F1) were immunized intramuscularly IM (prime) with a mix of (1×10$^{10}$ VP/vector) HAdV35.Empty.pIX-L2(S) 6.31.33.16 and HAdV35.Empty.pIX-L2(S)11.52/58.45.18, HAdV35.Empty.pIX-L2(S)6.31.33.16 alone, HAdV35.Empty.pIX-L2(S)11.52/58.45.18 alone, HAdV35.Empty.pIX-L2(S)45.18.16 alone (positive control) and HAdV35.Empty (negative control). At week 8 post prime, the mice were boosted with the same vector at the same concentration (1×10$^{10}$ VP/vector). At each two week interval, mice were bled and finally sacrificed at week 12 post prime (FIG. 4A). The humoral responses were measured using a 9-valent MSD ELISA assay (ELISA titer EC$_{50}$ Log$_{10}$). The antibody responses induced at week 8 post prime and week 12 (4 weeks post boost) against each HPV types 6, 11, 16, 18, 31, 33, 45 and 52/58 and HPV type 59 were measured. The data shows that after one administration of 1×10$^{10}$ VP/vector at week 8 (prime only): all single vectors and the mix of two vectors induce antibody responses against HPV types 6, 11, 16, 18, 31, 33, 45, 52/58 and 59, even if the HPV type (HPV 59) was not included in the vaccine (FIG. 4B). For each single vector and the mix of two vectors, the HPV type specific anti-L2 responses were boosted at week 12 (FIG. 4B). Even though the single vectors can induce immune responses against the types not included in the pIX-L2 concatemer, for instance the responses induced against the HPV type 6, 11 and 33 in mice immunized with HAdV35.Empty.pIX-L2(Sx3)45.18.16 vector, the responses do seem to be considerably lower at week 12 than either of the Sx4 vectors alone (HAdV35.Empty.pIX-L2(Sx4)11.52/58.45.18 or HAdV35.Empty.pIX-L2(Sx4)6.31.33.16) or the mix of two Sx4 vectors (FIG. 4B). Overall, the mix of two Sx4 vectors HAdV35.Empty.pIX-L2(Sx4)11.52/58.45.18 and HAdV35.Empty.pIX-L2(Sx4)6.31.33.16 induces a higher immune responses against all tested HPV types when compared to the HAd35.Empty.pIX-L2(Sx3)45.18.16 vector control and for some HPV types also higher immune responses than the single Sx4 vectors (HAdV35.Empty.pIX-L2(Sx4)11.52/58.45.18 or HAdV35.Empty.pIX-L2(Sx4) 6.31.33.16). Even though cross-reactive binding antibodies are generated by all pIX-L2 display vectors the higher antibody immune responses achieved with the 9-valent vector mix indicate the importance of including several L2 antigenic fragments from multiple HPV types.

Since HPV neutralizing antibody (nAb) responses in serum are considered a correlate of HPV protection (Pastrana et al., 2004), the capacity of pIX-L2 to induce nAb responses was determined. For this purpose, serum from immunized described above (FIG. 4A) were tested for HPV16, HPV18, HPV31 and HPV59 specific nAb responses in a HPV pseudovirions virus neturalization assay (VNA) and compared to the 4-valent Gardasil vaccinated mice in the assay.

HPV Pseudovirions Production and VNA

Figure 4C:
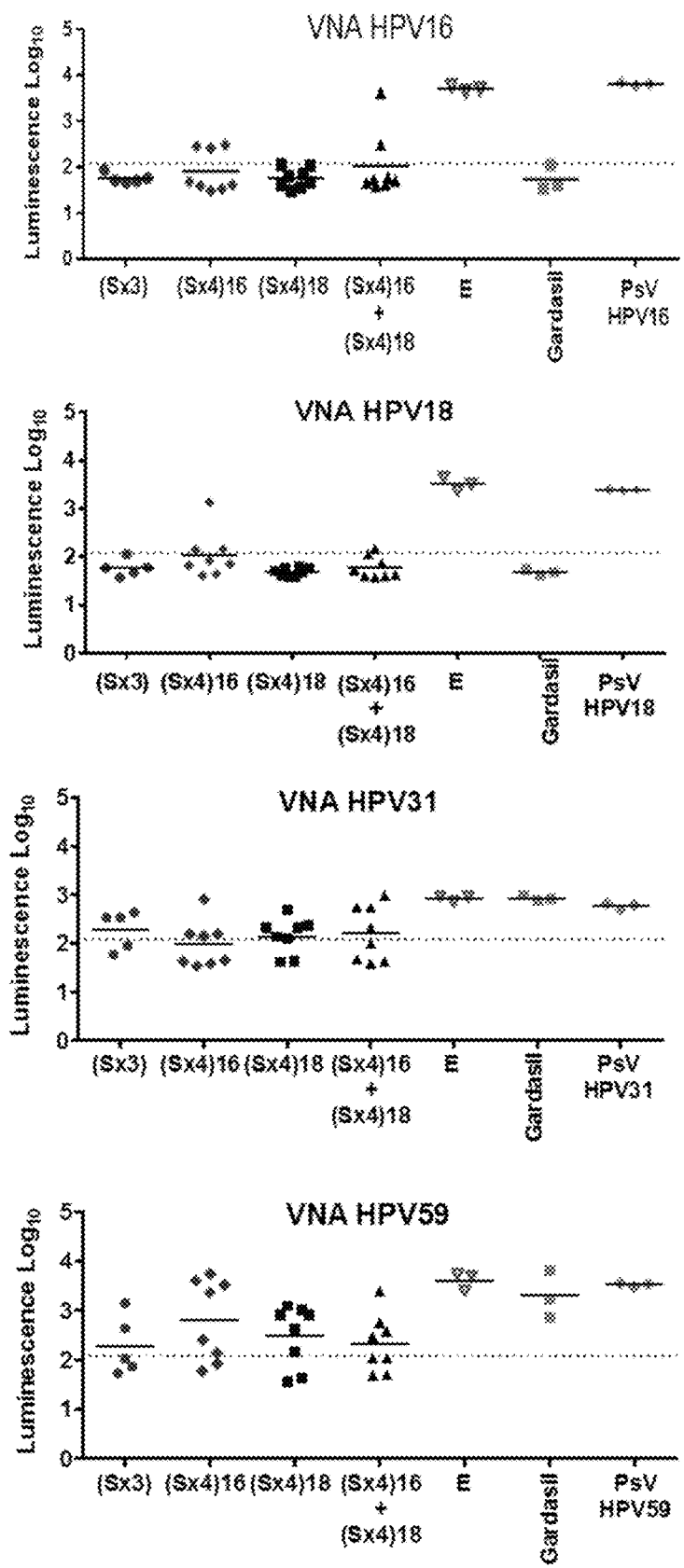

The HPV pseudovirions production and the VNA were essentially performed as previously described (Day et al., 2012), with the exception that recombinant Furin was used instead of the supernatant from Furin producing cells. In short, the HPV pseudovirions production HEK293FT cells were used (DMEM (Thermo Fisher)+10% Fetal Bovine Serum (FBS)). For this purpose transfection was performed with the HPV L1-L2 capsid-encoding pcDNA2004Neo(−) .HPVx.L1S.IRES.L2.WPRE plasmids and pCLucF plasmid encoding firefly luciferase and eGFP proteins. HPV pseudovirions encoding the luciferase gene were incubated with the serum from immunized mice prior to the cell transduction. As readout for the neutralization capacity relative light units (RLU) were measured using the Synergy Neo2 Multi-Mode Reader (BioTek).

nAb immune responses against HPV16 and HPV18 were induced by the single vectors and by the mix, and the responses were comparable to the response induced by the quadrivalent-Gardasil (HPV 6, 11, 16 and 18) (FIG. 4C). Also the HPV31 and 59 nAb neutralization titers were induced by all L2 display vectors (FIG. 4C). In conclusion, all pIX-L2 display vectors induced HPV type specific nAb immune responses of which the HPV16 and HPV18 immune responses were comparable to the 4-valent Gardasil.

Example 3: Generation of Genetically Stable pIX-L2(Sx4) Modified Vectors in the PER.C6® Producer Cell Line Even though adenoviral vectors are considered genetically stable, (Bett, Prevec, & Graham, 1993; King, Teertstra, Blanco, Salas, & van der Vliet, 1997) mutations and/or deletions have been observed, usually when the deletion mutants present a selective growth advantage (Harro et al., 2009). Due to the relatively high homology (~65-70%) between the different HPV types in the L2 protein 10-40 amino acids concatemers, encoded in the HAdV genome, genetic instability during the vector generation might occur (Bzymek & Lovett, 2001).

Figure 5A:
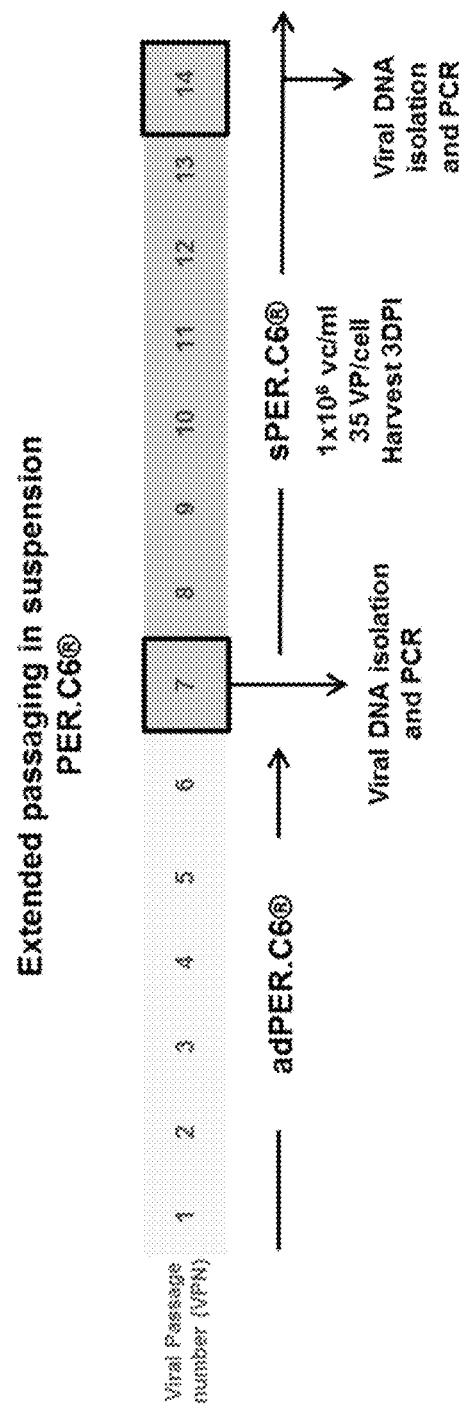
Figure 5B:
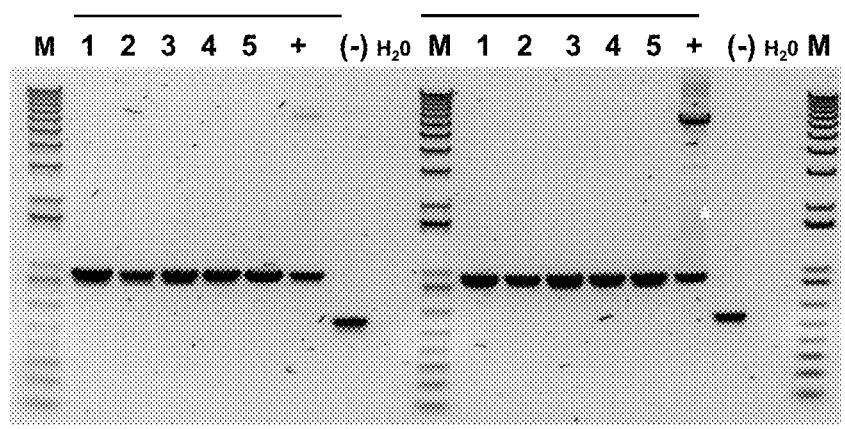

To determine the genetic stability profile of the pIX-modified vectors encoding the highly repetitive L2 concatemers upon production in the producer PER.C6® cells, five clones (i.e. plaques) were passaged in PER.C6® cells up to four viral passages (VPN) beyond the envisioned commercial process. An extended passaging assay followed by PCR amplification of the pIX-modified region to assess the genetic stability was performed as previously described by Vogels et al. (Vogels et al., 2007)). Instead of performing the passaging in adherent PER.C6® (ad)PER.C6® cells only, at viral passage number 7 (VPN7) the extended passaging was continued in PER.C6® cells in suspension)(sPER.C6® (FIG. 5A). The passaging in sPER.C6® cells was performed under controlled conditions at a fixed 35 VP/cell (HAdV35) and harvested 3 days post infection (DPI) for each passage. The viral DNA was isolated at VPN 7 and VPN 14 in order to determine the integrity of the pIX-region. The HAdV35 vectors containing the pIX-L2(Sx4) concatemers were generated as indicated above by the transfection of three plasmids, nonetheless the effects of the highly repetitive L2 concatemer might have a detrimental effect on the genetic stability of the pIX-L2 during the vector production. In order to mitigate the effects of the L2 homology within the Sx4 concatemers on genetic level, the L2 concatemers were synthesized (GeneArt) by reducing the homology on DNA level using codon optimization for mammalian protein expression. This custom codon optimization resulted in a reduction of an overall homology of ~2-3% while still retaining the optimal codon usage for the expression in mammalian cells. Five plaques (n=5) of the HAdV35.Empty.pIX-L2(S)6.31.33.16 and HAdV35.Empty.pIX-L2(S)11.52/58.45.18 vectors were passaged up to VPN 14 (FIG. 5B). The non-reduced pIX-L2(Sx4) HAdV35 (i.e. codon optimized but no inter HPV type 10-40 amino acid fragment homology reduction) were also found genetically stable after extended passaging (Table 2). Regardless of the L2 homology (reduced vs. non-reduced) in the Sx4 concatemers all the clones of the HAdV35 pIX-L2(Sx4) vectors remained genetically stable during extended passaging in PER.C6® cells. Additionally, the small purified vector preparations described above of the (reduced L2 concatemer homology) HAdV35.Empty.pIX-L2(S)6.31.33.16 and HAdV35.Empty.pIX-L2(S)11.52/58.45.18 vectors were tested for genetic stability by PCR as well and shown to be genetically stable, indicating that 'the scale' up during the vector production yields genetically stable pIX-L2 vectors. Taken together, despite the highly repetitive nature of the genetically encoded L2 concatemers fused to protein IX, the vectors remain genetically stable in the PER.C6® cells.

tored near-consensus HIV type 1 clade B gag vaccines in healthy adults. *AIDS Res Hum Retroviruses*, 25(1), 103-114. doi: 10.1089/aid.2008.0212

Karanam, B., Jagu, S., Huh, W. K., & Roden, R. B. (2009). Developing vaccines against minor capsid antigen L2 to prevent papillomavirus infection. *Immunol Cell Biol*, 87(4), 287-299. doi: 10.1038/icb.2009.13

King, A. J., Teertstra, W. R., Blanco, L., Salas, M., & van der Vliet, P. C. (1997). Processive proofreading by the adenovirus DNA polymerase. Association with the priming protein reduces exonucleolytic degradation. *Nucleic Acids Res*, 25(9), 1745-1752.

Munoz, N., Bosch, F. X., Castellsague, X., Diaz, M., de Sanjose, S., Hammouda, D., Meijer, C. J. (2004). Against which human papillomavirus types shall we vaccinate and screen? The international perspective. *Int J Cancer*, 111 (2), 278-285. doi: 10.1002/ijc.20244

Parkin, D. M., & Bray, F. (2006). Chapter 2: The burden of HPV-related cancers. *Vaccine*, 24 Suppl 3, S3/11-25. doi: 10.1016/j.vaccine.2006.05.111

Roden, R. B., Day, P. M., Bronzo, B. K., Yutzy, W. H. th, Yang, Y., Lowy, D. R., & Schiller, J. T. (2001). Positively charged termini of the L2 minor capsid protein are necessary for papillomavirus infection. *J Virol*, 75(21), 10493-10497. doi: 10.1128/JVI.75.21.10493-10497.2001

TABLE 2

Genetic stability pIX-L2 capsid display vectors in the producer cell lines PER.C6 ®.

| | Capsid modification | | pIX fusion | Genetic stability pIX | |
|---|---|---|---|---|---|
| | E1-region | pIX | a.a. | VPN 7 | VPN 14# |
| HAdV26 Advac © | Empty | 33.31.45.18.16 (S × 5) | 153 | Stable | Stable |
| | Empty | 52.31.45.18.16 (S × 5) | 153 | Stable^ | Stable^ |
| | Empty | 33.45.18.16 (S × 4) | 123 | Stable | Stable |
| | Empty | 31.45.18.16 (S × 4) | 123 | Multiple bands* | Multiple bands* |
| | Empty | 45.18.16 (S × 3) | 93 | Multiple bands* | Multiple bands* |
| HAdV35 Advac © | Empty | 6.31.33.16 (S × 4) | 123 | Stable | Stable |
| | Empty | 11.52/58.45.18 (S × 4) | 123 | Stable | Stable |
| Batch 2 | Empty | 6.31.33.16 (S × 4) | 123 | Stable | Stable |
| Batch 2 | Empty | 11.52/58.45.18 (S × 4) | 123 | Stable | Stable |
| | Empty | (NR) 6.31.33.16 (S × 4) | 123 | Stable | Stable |
| | Empty | (NR) 11.52/58.45.18 (S × 4) | 123 | Stable | Stable |
| | ΔCMV.pA | 6.31.33.16 (S × 4) | 123 | Stable | Stable |
| | ΔCMV.pA | 11.52/58.45.18 (S × 4) | 123 | Stable | Stable |
| | Empty | 45.18.16 (S × 3) | 93 | Stable | Stable |

*multiple bands in PCR: mixed population despite as a consequence of the homologous recombination by the two plasmid system,
NR: non-reduced inter-epitope homology,
: confirmed by sequencing,
^: confirmed by whole genome.

REFERENCES

Bett, A. J., Prevec, L., & Graham, F. L. (1993). Packaging capacity and stability of human adenovirus type 5 vectors. *J Virol*, 67(10), 5911-5921.

Bzymek, M., & Lovett, S. T. (2001). Instability of repetitive DNA sequences: the role of replication in multiple mechanisms. *Proc Natl Acad Sci USA*, 98(15), 8319-8325. doi: 10.1073/pnas.111008398

Hanna Seitz, Martin Müller. (2014). Current Perspectives on HPV Vaccination A Focus on Targeting the L2 Protein. *Future Virology*, 9(7), 633-653.

Harro, C. D., Robertson, M. N., Lally, M. A., O'Neill, L. D., Edupuganti, S., Goepfert, P. A., Merck, V. Study Teams. (2009). Safety and immunogenicity of adenovirus-vec- Rosa-Calatrava, M., Grave, L., Puvion-Dutilleul, F., Chatton, B., & Kedinger, C. (2001). Functional analysis of adenovirus protein IX identifies domains involved in capsid stability, transcriptional activity, and nuclear reorganization. *J Virol*, 75(15), 7131-7141. doi: 10.1128/JVI.75.15.7131-7141.2001

Schiller, J. T., & Lowy, D. R. (2012). Understanding and learning from the success of prophylactic human papillomavirus vaccines. *Nat Rev Microbiol*, 10(10), 681-692. doi: 10.1038/nrmicro2872

Smith, J. S., Lindsay, L., Hoots, B., Keys, J., Franceschi, S., Winer, R., & Clifford, G. M. (2007). Human papillomavirus type distribution in invasive cervical cancer and high-grade cervical lesions: a meta-analysis update. Int J Cancer, 121(3), 621-632. doi: 10.1002/ijc.22527

Vellinga, J., M. J. W. E. Rabelink, S. J. Cramer, D. J. M. Van der Wollenberg, H. Van der Meulen, K. N. Leppard, F. J. Fallaux, R. C. Hoeben. 2004. Spacers Increase the Accessibility of Peptide Ligands Linked to the Carboxyl Terminus of Adenovirus Minor Capsid Protein IX. Journal of Virology, April 2004, p. 3470-3479, Vol. 78, No. 7.

Vogels, R., Zuijdgeest, D., van Meerendonk, M., Companjen, A., Gillissen, G., Sijtsma, J., Havenga, M. J. (2007). High-level expression from two independent expression cassettes in replication-incompetent adenovirus type 35 vector. *J Gen Virol,* 88(Pt 11), 2915-2924. doi: 10.1099/vir.0.83119-0

```
SEQUENCE LISTING
Sx3 HPV 45.18.16 (10-40 residues of L2 protein)
                                                 SEQ ID NO: 1
KRASATDLYRTCKQSGTCPPDVINKVEGTTKRASVTDLYKTCKQSGTC

PPDVVPKVEGTTKRASATQLYKTCKQAGTCPPDIIPKVEGKT

Sx4 HPV 31.45.18.16 (10-40 residues of L2
protein)
                                                 SEQ ID NO: 2
KRASATQLYQTCKAAGTCPSDVIPKIEHTTKRASATDLYRTCKQSGTC

PPDVINKVEGTTKRASVTDLYKTCKQSGTCPPDVVPKVEGTTKRASAT

QLYKTCKQAGTCPPDIIPKVEGKT

Sx4 HPV 33.45.18.16 (10-40 residues of L2
protein)
                                                 SEQ ID NO: 3
KRASATQLYQTCKATGTCPPDVIPKVEGSTKRASATDLYRTCKQSGTC

PPDVINKVEGTTKRASVTDLYKTCKQSGTCPPDVVPKVEGTTKRASAT

QLYKTCKQAGTCPPDIIPKVEGKT

Sx5 HPV 31.33.45.18.16 (10-40 residues of L2
protein)
                                                 SEQ ID NO: 4
KRASATQLYQTCKAAGTCPSDVIPKIEHTTKRASATQLYQTCKATGTC

PPDVIPKVEGSTKRASATDLYRTCKQSGTCPPDVINKVEGTTKRASVT

DLYKTCKQSGTCPPDVVPKVEGTTKRASATQLYKTCKQAGTCPPDIIP

KVEGKT

Sx5 HPV 52/58.31.45.18.16 (10-40 residues of L2
protein)
                                                 SEQ ID NO: 5
KRASATQLYQTCKASGTCPPDVIPKVEGTTKRASATQLYQTCKAAGTC

PSDVIPKIEHTTKRASATDLYRTCKQSGTCPPDVINKVEGTTKRASVT

DLYKTCKQSGTCPPDVVPKVEGTTKRASATQLYKTCKQAGTCPPDIIP

KVEGKT

Sx4 HPV 6.31.33.16 (10-40 residues of L2
protein)
                                                 SEQ ID NO: 6
KRASATQLYQTCKLTGTCPPDVIPKVEHNTKRASATQLYQTCKAAGTC

PSDVIPKIEHTTKRASATQLYQTCKATGTCPPDVIPKVEGSTKRASAT

QLYKTCKQAGTCPPDIIPKVEGKT

Sx4 HPV 11.52/58.45.18 (10-40 residues of L2
protein)
                                                 SEQ ID NO: 7
KRASATQLYQTCKATGTCPPDVIPKVEHTTKRASATQLYQTCKASGTC

PPDVIPKVEGTTKRASATDLYRTCKQSGTCPPDVINKVEGTTKRASVT

DLYKTCKQSGTCPPDVVPKVEGTT

Sx4 HPV 31(11-40).45(60-89).18(100-129).
16(101-130)
                                                 SEQ ID NO: 8
KRASATQLYQTCKAAGTCPSDVIPKIEHTTGTGSGSGGRTGYVPLGGR

SNTVVDVGPTRPDPSIVTLIEDSSVVTSGAPRPTFTGTSGFDSDPSIV

SLVEETSFIDAGAPTSVPSIPPDV (Spacer 1)
                                                 SEQ ID NO: 9
CNGTDAKIKLIKQELDKYKNAVTELQLLMQST (Spacer 2)
                                                 SEQ ID NO: 10
TNEKFHQIEKEFSEVEGRIQDLEKYVEDTKIDL (Spacer 3)
                                                 SEQ ID NO: 11
QTNARAIAAMKNSIQATNRAIFEVKEGTQQ (HAdV-35 pIX)
                                                 SEQ ID NO: 12
MSGNASFKGGVFSPYLTGRLPSWAGVRQNVMGSTVDGRPVQPANSSTL

TYATLSSSPLDAAAAAAAASVAANTVLGMGYYGSIVANSTSSNNPSTL

TQDKLLVLLAQLEALTQRLGELSQQVAELRVQTESAVGTAKSK (HAdV-26 pIX)
                                                 SEQ ID NO: 13
MNGTGGAFEGGLFSPYLTTRLPGWAGVRQNVMGSTVDGRPVLPANSST

MTYATVGNSSLDSTAAAAAAAAAMTATRLASSYMPSSGSSPSVPSSII

AEEKLLALLAELEALSRQLAALTQQVSELREQQQQQNK (epitope 1)
                                                 SEQ ID NO: 14
QLY + TCKQAGTCPPD (epitope 2)
                                                 SEQ ID NO: 15
RTGYIPLGTRPPT (epitope 3)
                                                 SEQ ID NO: 16
LVEETSFIDAGAP
```

The invention claimed is:

1. A recombinant adenoviral vector encoding a polypeptide comprising a capsid protein IX fused to an antigen, wherein said antigen comprises the amino acid sequence of SEQ ID NO: 1, SEQ ID NO: 2, SEQ ID NO: 3, SEQ ID NO: 4, SEQ ID NO: 5, SEQ ID NO: 6, or SEQ ID NO: 7.

2. The recombinant adenoviral vector according to claim 1, wherein the antigen comprises the amino acid sequence of SEQ ID NO: 3.

3. The recombinant adenoviral vector according to claim 1, wherein the antigen comprises the amino acid sequence of SEQ ID NO: 5.

4. The recombinant adenoviral vector according to claim 1, wherein said antigen comprises the amino acid sequence of SEQ ID NO: 6.

5. The recombinant adenoviral vector according to claim 1 wherein said antigen comprises the amino acid sequence of SEQ ID NO:1.

6. The recombinant adenoviral vector according claim 1, wherein said antigen comprises SEQ ID NO: 7.

7. The recombinant adenoviral vector according to claim 1, wherein said antigen comprises the amino acid sequence of SEQ ID NO: 2.

8. The recombinant adenoviral vector according to claim 1, wherein said antigen comprises the amino acid sequence of SEQ ID NO:4.

9. A recombinant adenoviral vector encoding a polypeptide comprising a capsid protein IX fused to an antigen, wherein said antigen comprises 4 consecutive amino acid motifs of about 20 to about 40 amino acids, wherein the first motif comprises the amino acid residues 17-36 of a HPV L2 protein of the HPV type 31, the second motif comprises the amino acid residues 69-81 of a HPV L2 protein of the HPV type 45, the third motif comprises the amino acid residues 108-121 of a HPV L2 protein of the HPV type 18, and the fourth motif comprises the amino acid residues 108-121 of a HPV L2 protein of the HPV type 16.

10. The recombinant adenoviral vector according to claim 9, wherein said antigen comprises the amino acid sequence of SEQ ID NO:8.

11. The recombinant adenoviral vector according to claim 1, wherein the protein IX and the antigen are linked together by a linker or a spacer.

12. The recombinant adenoviral vector according to claim 11, wherein the linker comprises an amino acid sequence having 3 consecutive flexible residues of glycine.

13. The recombinant adenoviral vector according to claim 1, wherein said vector is selected from the group consisting of: HAdV4, HAdV11, HAdV26, HAdV35, HAdV48, HAdV49, HAdV50, non-human primate vectors and chimeric vectors.

14. The recombinant adenoviral vector according to claim 11, wherein said adenoviral vector is a HAdV26 or HAdV35.

15. The recombinant adenoviral vector according to claim 1, wherein said vector further comprises a nucleic acid encoding one or more heterologous proteins as a transgene.

16. A composition comprising a combination of at least two different recombinant adenoviral vectors according to claim 1.

17. A composition comprising two recombinant adenoviral vectors according to claim 1, wherein the antigen of said first vector comprises the amino acid sequence of SEQ ID NO:6 and the antigen of said second vector comprises the amino acid sequence of SEQ ID NO:7.

18. A vaccine comprising a recombinant adenoviral vector according to claim 1, further comprising a pharmaceutically acceptable excipient.

19. A method of inducing an immune response in a subject, comprising administering the vaccine of claim 18 to said subject.

20. The recombinant adenoviral vector according to claim 9, wherein the protein IX and the antigen are linked together by a linker or a spacer.

21. The recombinant adenoviral vector according to claim 20, wherein the linker comprises an amino acid sequence having 3 consecutive flexible residues of glycine.

22. The recombinant adenoviral vector according to claim 9, wherein said vector is selected from the group consisting of: HAdV4, HAdV11, HAdV26, HAdV35, HAdV48, HAdV49, HAdV50, non-human primate vectors and chimeric vectors.

23. The recombinant adenoviral vector according to claim 9, wherein said vector further comprises a nucleic acid encoding one or more heterologous proteins as a transgene.

24. A vaccine comprising a recombinant adenoviral vector according to claim 9, further comprising a pharmaceutically acceptable excipient.

25. A method of inducing an immune response in a subject, comprising administering the vaccine of claim 24 to said subject.

* * * * *